(12) United States Patent
Vidal et al.

(10) Patent No.: US 7,776,107 B2
(45) Date of Patent: Aug. 17, 2010

(54) AMINOINDOLIZINES, DYEING COMPOSITION COMPRISING AT LEAST ONE AMINOINDOLIZINE, METHODS AND USES THEREOF

(75) Inventors: Laurent Vidal, Paris (FR); Eric Metais, Saint-leu-la-Foret (FR); Aziz Fadli, Chelles (FR); Alan Katritzky, Gainsville, FL (US)

(73) Assignee: L'Oreal S.A., Paris (FR)

( * ) Notice: Subject to any disclaimer, the term of this patent is extended or adjusted under 35 U.S.C. 154(b) by 15 days.

(21) Appl. No.: 12/341,453

(22) Filed: Dec. 22, 2008

(65) Prior Publication Data

US 2009/0235467 A1    Sep. 24, 2009

(30) Foreign Application Priority Data

Dec. 20, 2007   (FR) .................................. 07 60136

(51) Int. Cl.
*A61Q 5/10* (2006.01)
*C07D 221/02* (2006.01)

(52) U.S. Cl. ...................... 8/405; 8/406; 8/407; 8/408; 8/409; 8/410; 8/412; 8/435; 546/112

(58) Field of Classification Search ...................... 8/405, 8/406, 407, 408, 409, 410, 412, 435; 546/112
See application file for complete search history.

(56) References Cited

U.S. PATENT DOCUMENTS 6,572,664 B2 * 6/2003 Breton et al. .................. 8/405
2002/0002749 A1    1/2002 Breton et al.

FOREIGN PATENT DOCUMENTS

| EP | 1 129 691 A2 | 9/2001 |
| GB | 2 075 540 A | 11/1981 |
| JP | 1-260646 | 10/1989 |

OTHER PUBLICATIONS

STIC Search Report dated Jan. 25, 2010.*

Database CA [Online]; Chemical Abstracts Service, Columus, Ohio, US; Eiji Ochiai et al., XP002497274.

Yoshinori Tominaga et al., "Synthesis of 2-Methylthioindolizine-3-carbonitriles Using Nitro Ketene Dithioacetal," Journal of Heterocyclic Chemistry, vol. 25, No. 6, pp. 1745-1749 (1988).

Martino Colonna et al., "Synthesis and Oxidation of Symmetrical Azo-compounds Derived From Indolizines," Gazzetta Chimica Italiana, vol. 101, No. 5, pp. 396-409 (1971).

T. Melton et al., "Indolizines. Part IV. Synthesis from 2-Acylmethylene-1-benzyl-1,2-dihydropyridine, Phenyl-2-picolyl Sulphone, and Related Compounds," Journal of the Chemical Society, Section C: Organic Chemistry, Chemical Society, Letchworth, GB, vol. 167, No. 10, pp. 983-988 (1967).

J. Hurst et al., "Indolizines. Part III," Journal of the Chemical Society, pp. 2948-2955 (1965).

English language abstract of JP 1-260646, Oct. 17, 1989.

French Search Report for FR 0760136, dated Sep. 25, 2008.

\* cited by examiner

*Primary Examiner*—Eisa B Elhilo
(74) *Attorney, Agent, or Firm*—Finnegan, Henderson, Farabow, Garrett & Dunner LLP

(57) ABSTRACT

A new class of chemical entities chosen from aminoindolizines of formula (I), acid addition salts thereof, and solvates thereof:

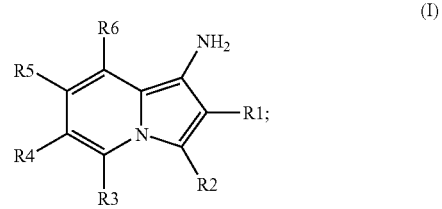

their use for dyeing keratin fibers, including human keratin fibers such as the hair; dyeing compositions comprising such chemical entities; and to kits containing compositions comprising those chemical entities.

25 Claims, No Drawings

AMINOINDOLIZINES, DYEING COMPOSITION COMPRISING AT LEAST ONE AMINOINDOLIZINE, METHODS AND USES THEREOF

This application claims benefit of priority under 35 U.S.C. §119 to French Patent Application No. FR 0760136, filed Dec. 20, 2007, the contents of which are incorporated herein by reference.

Disclosed herein are new aminoindolizines, their use for dyeing keratin fibers, including human keratin fibers such as the hair, dyeing compositions comprising such aminoindolizines, and the methods employing these aminoindolizines.

It is known practice to dye keratin fibers, including the human hair, with dyeing compositions containing oxidation dye precursors, generally called oxidation bases, such as ortho- or para-phenylenediamines, ortho- or para-aminophenols and heterocyclic compounds. These oxidation bases are colorless or weakly colored compounds which, when combined with oxidizing products, may be able to produce colored compounds by a process of oxidative condensation.

It is also known that the shades obtained with these oxidation bases can be varied by combining them with couplers or coloration modifiers, the latter being chosen for example, from aromatic meta-diaminobenzenes, meta-aminophenols, meta-diphenols and certain heterocyclic compounds such as indole compounds.

The variety of molecules employed as oxidation bases and couplers can allow a rich palette of colors to be obtained.

It is desired that the "permanent" coloration obtained by virtue of these oxidation dyes, moreover, can meet at least one of a certain number of demands. Thus it should have no toxicological drawbacks, it should allow shades to be obtained in the desired intensity, and, if possible, it should be highly resistant to external agents such as light, weathering, washing, perming treatments, perspiration and rubbing.

It is desired that the dyes should also allow grey hair to be covered and, finally, should be as unselective as possible: that is, they should make it possible to produce minimal differences in coloration along a single keratin fiber, which in general is differently sensitized (i.e. damaged) between its tip and its root.

Surprisingly and beneficially, the Inventors have now discovered that it is possible to obtain new compositions for dyeing keratin fibers, including human keratin fibers such as the hair, which are capable of producing colorations with at least one of the benefits described above. For example, by the use of at least one aminoindolizine, the colorations may be at least one of varied shades which can be powerful, attractive, and relatively unselective and which may effectively withstand the various attacks to which the fibers may be subjected.

Moreover, these compositions exhibit a good toxicological profile.

Accordingly, one aspect of the present disclosure is a class of aminoindolizines, as well as processes for their synthesis.

Another aspect of the present disclosure is a composition comprising at least one aminoindolizine, the dyeing methods employing this composition, the uses of said composition according to the present disclosure for dyeing keratin fibers, including human keratin fibers such as the hair, and, in addition, multi-compartment devices or kits for dyeing.

The composition of the present disclosure can make it possible, for example, to obtain a keratin-fiber coloration which can be very powerful, relatively unselective and can be highly persistent, for instance to light.

At least one other feature, aspect, object, and benefit of the present disclosure may emerge even more clearly from a reading of the description and examples which follow.

The present disclosure relates to at least one chemical entity chosen from aminoindolizines of formula (I), acid addition salts thereof, and solvates thereof:

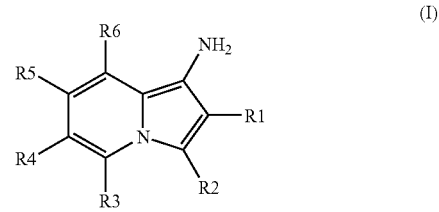

wherein
$R_1$ is a radical chosen from:
linear and branched $C_1$-$C_{10}$ alkyl radicals which are optionally substituted by at least one group chosen from OH and $OR_{19}$ groups, wherein $R_{19}$ is chosen from linear and branched $C_1$-$C_6$ alkyl radicals optionally substituted by at least one OH radical,
sulphur-containing radicals chosen from SR and $SO_2Me$, R being chosen from linear and branched $C_1$-$C_6$ alkyl radicals and aryl radicals,
nitrogen-containing radicals chosen from $NH_2$, $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino, $C_1$-$C_6$ mono- and dialkylamino, carboxamido, ureido and guanidinyl groups, and optionally interrupted by an oxygen atom or at least one $N(R_{13})$ group, $R_{13}$ being chosen from a hydrogen atom and $C_1$-$C_6$ alkyl radicals, it being possible for the radicals $R_7$ and $R_8$ to form, together with the nitrogen atom to which they are attached, a saturated or unsaturated heterocycle containing 5 to 7 ring members,
radicals $OR_9$, $R_9$ being chosen from linear and branched $C_1$-$C_6$ alkyl radicals optionally substituted by at least one OH radical, and from linear and branched $C_1$-$C_6$ alkoxy radicals,
radicals chosen from COOH, $CONH_2$, $CONHR_1$, and $CONR_{11}R_{12}$, $R_{11}$ and $R_{12}$, which are identical or different, being chosen from linear and branched $C_1$-$C_6$ alkyl radicals optionally interrupted by at least one $N(R_{14})$ group, $R_{14}$ being chosen from a hydrogen atom and $C_1$-$C_6$ alkyl radicals optionally substituted by a hydroxyl group, it being possible for the radicals $R_{11}$ and $R_{12}$ to form, together and with the nitrogen atom to which they are attached, a saturated or unsaturated heterocycle containing 5 to 7 ring members;
$R_2$ is a radical chosen from:
linear and branched $C_1$-$C_6$ alkyl radicals,
hydrogen atoms,
radicals chosen from COOH, CN, $CF_3$ and alkoxycarbonyl $COOR_{10}$, $R_{10}$ being chosen from linear and branched $C_1$-$C_6$ alkyl radicals, and aryl and heteroaryl radicals,
radicals chosen from $CONH_2$, $CONHR_{11}$ and $CONR_{11}R_{12}$,
the radicals $OR_9$, and
radicals SR, SOR and $SO_2R$,
wherein R, $R_9$, $R_{11}$, and $R_{12}$ are as defined above,
$R_3$, $R_4$, $R_5$ and $R_6$, independently of one another, are chosen from:

aryl and heteroaryl, and linear and branched $C_1$-$C_6$ alkyl radicals optionally interrupted by at least one entity chosen from $N(R_{13})$ groups and oxygen, the radicals $OR_9$, hydrogen atoms, halogens chosen from fluorine, chlorine and bromine, nitrogen-containing radicals chosen from $NH_2$, $NHR_7$ and $NR_7R_8$, COOH and CN radicals and alkoxycarbonyl radicals $COOR_{10}$, where $R_7$, $R_8$, $R_9$ and $R_{10}$ are as defined above, with the proviso that not more than one of the radicals $R_1$, $R_3$, $R_4$, $R_5$ and $R_6$ represents a nitrogen-containing radical chosen from $NH_2$, $NHR_7$ and $NR_7R_8$.

For example, $R_1$ can be chosen from:

linear and branched $C_1$-$C_{10}$, such as $C_1$-$C_6$ and $C_1$-$C_4$ alkyl radicals, the sulphur-containing radical $SO_2Me$, nitrogen-containing radicals chosen from $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino and $C_1$-$C_6$ mono- and dialkylamino groups, such as chosen from hydroxyl and $C_1$-$C_4$ mono and dialkylamino groups.

For example, in at least one embodiment, $R_1$ can be chosen from: —$CH_3$, —$SO_2CH_3$, —$NH(CH_3)$, —$N(CH_2CH_2OH)_2$, —$N(CH_3)_2$, —$NH(CH_2CH_2OH)$, —$NH(CH_2CH_2N(CH_3)_2)$, —$NH(CH_2CH_3)$, and —$NH(CH_2CH_2CH_2N(CH_3)_2)$.

The radical $R_2$ can be, for instance, chosen from:

linear and branched $C_1$-$C_6$, such as $C_1$-$C_4$ alkyl radicals, hydrogen atoms, radicals chosen from COOH, CN, $CF_3$ and alkoxycarbonyl $COOR_{10}$, $R_{10}$ being chosen from linear and branched $C_1$-$C_6$ alkyl radicals, radicals chosen from $CONH_2$, $CONHR_{11}$ and $CONR_{11}R_{12}$, the radicals $OR_9$, and the radicals SR and $SO_2R$.

For example, in at least one embodiment, the radical $R_2$ can be chosen from hydrogen atoms and the radicals: —$CH_3$, —$COOCH_3$, —$COOCH_2CH_3$, —CN, —$CF_3$, —CONH($CH_2CH_3$), —$CONH(CH_2CH_2CH_2N(CH_3)_2)$, —$CON(CH_3)_2$, —$CONH(CH_2CH_2OH)$, —$CONH_2$, —$OCH_3$, —$SCH_3$, and —$SO_2CH_3$.

The radicals $R_3$, $R_4$, $R_5$ and $R_6$, independently of one another, can be chosen, for instance, from:

hydrogen atoms, the radicals $OR_9$, $R_9$ being chosen from $C_1$-$C_4$ alkyl radicals, for example, —$OCH_3$, —$NH_2$ radicals, with the proviso that not more than one of the radicals $R_1$, $R_3$, $R_4$, $R_5$ and $R_6$ is an —$NH_2$ radical.

The aminoindolizines of formula (I) may be present in free form or in the form of salts, such as addition salts with an organic or inorganic acid, which can be chosen, for example, from hydrochlorides, hydrobromides, sulphates, citrates, succinates, tartrates, lactates, tosylates, benzenesulphonates, phosphates and acetates.

Non-limiting examples of the aminoindolizines of formula (I) include the compounds:

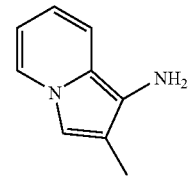

A

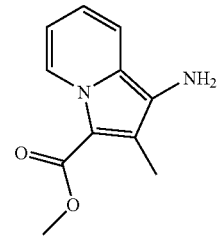

B

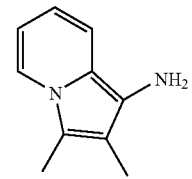

C

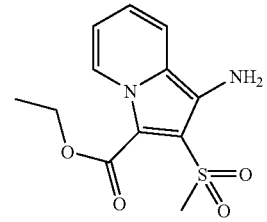

D

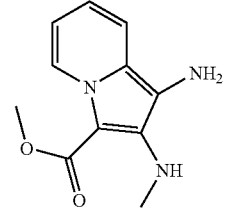

E

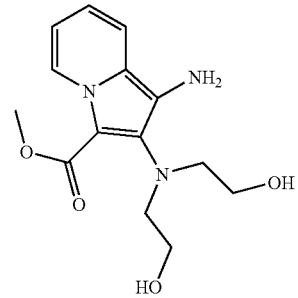

F

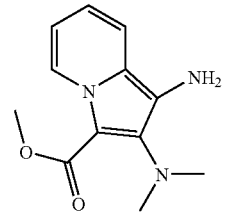

G

-continued
H
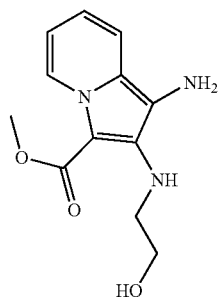
I
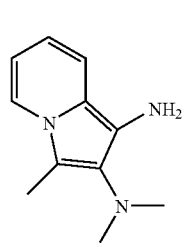
J
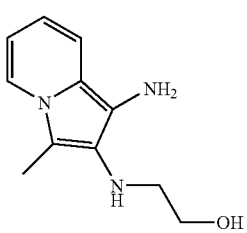
K
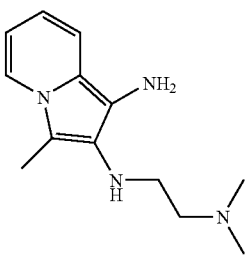
L
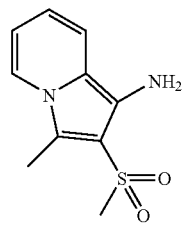
M
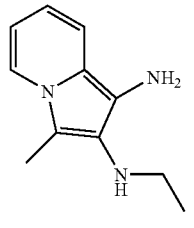
-continued
N
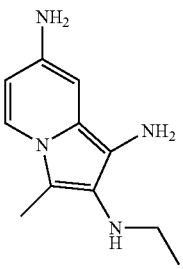
O
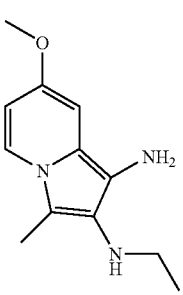
P
Q
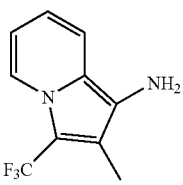
R
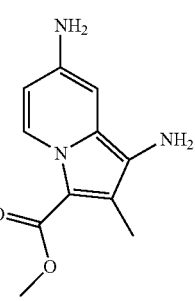
S
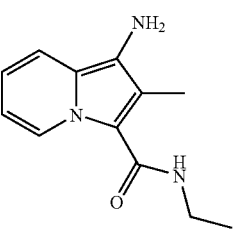

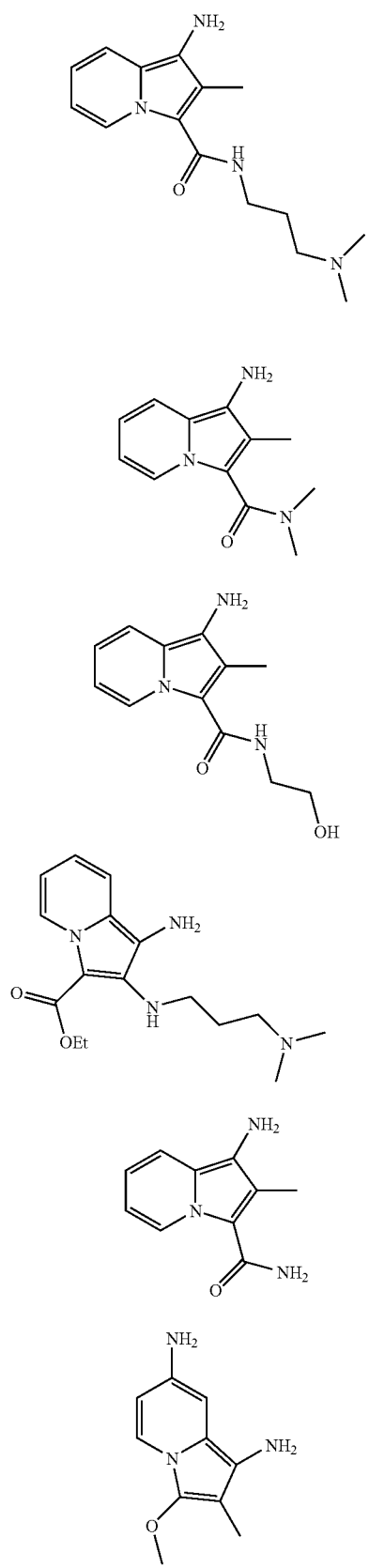

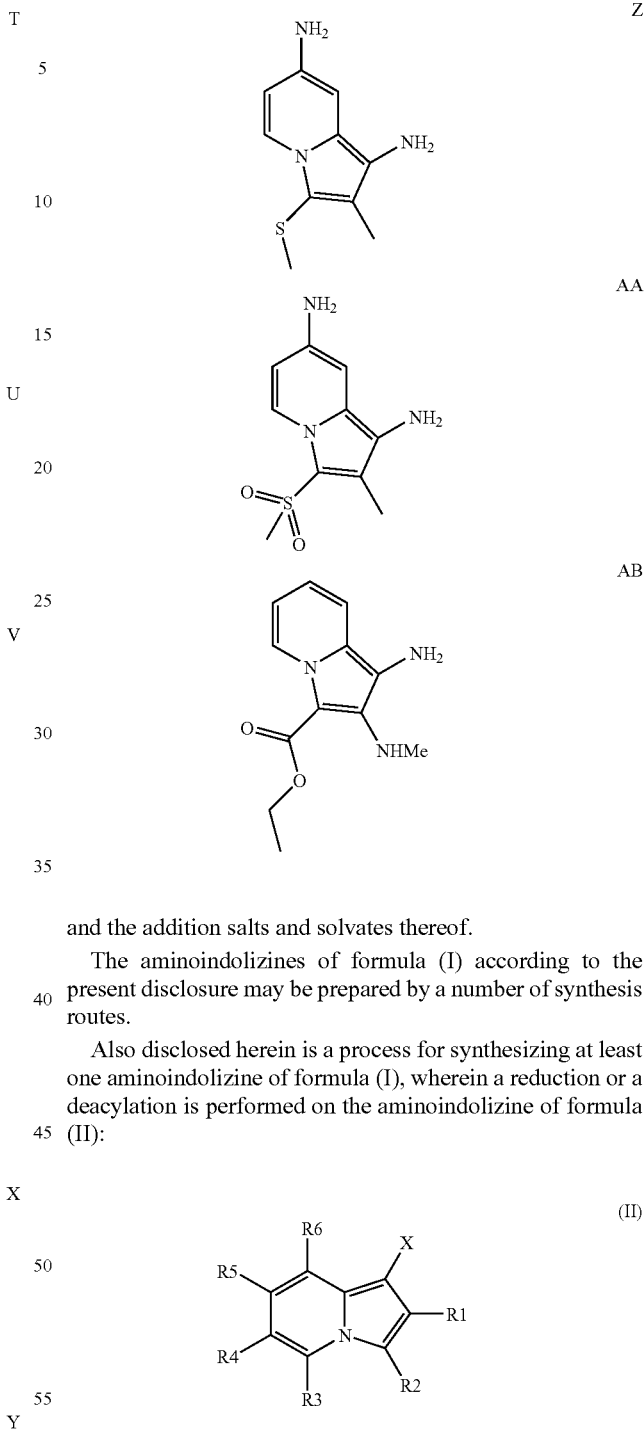

and the addition salts and solvates thereof.

The aminoindolizines of formula (I) according to the present disclosure may be prepared by a number of synthesis routes.

Also disclosed herein is a process for synthesizing at least one aminoindolizine of formula (I), wherein a reduction or a deacylation is performed on the aminoindolizine of formula (II):

wherein

X is chosen from nitro, nitroso, arylazo and heteroarylazo radicals, radicals $NHCOR_{15}$, $R_{15}$ being chosen from linear and branched $C_1$-$C_6$ alkyl, and aryl and heteroaryl radicals, $R_1$, $R_2$, $R_3$, $R_4$, $R_5$ and $R_6$ are as defined above.

Method of making the at least one aminoindolizine of formula (I) via condensation with an alpha-haloketone or alpha-alkoxyketone with an alpha-picoline derivative Scheme I:

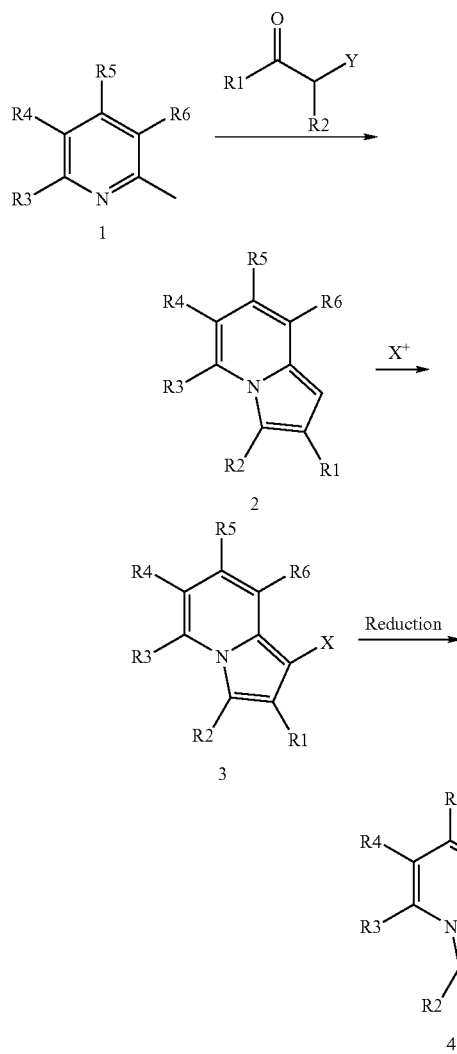

The first step involves condensing a ketone bearing a halogen (Y) in alpha position with an alpha-picoline derivative 1 (Batroff V.; Flitsch W., Liebigs Annalen der Chemie, 1987, (7), p. 621). The indolizine 2 obtained reacts with any amine-precursor electrophile $X^+$ chosen from $NO^+$, $NO_2^+$, $ArN_2^+$ and $HetArN_2^+$ type, to give the compounds (3). The latter is hydrogenated by heterogeneous catalyst(s), such as Pd/C, Pd(II)/C, Ni/Ra, etc., or is reduced by a metal such as zinc, iron, tin, etc. (see Advanced Organic Chemistry, 3rd edition, J. March, and Reduction in organic Chemistry, M; Hudlicky) to give the indolizines (4).

It being understood that:

X is chosen from:

nitro, nitroso and arylazo and heteroarylazo radicals; and $R_1$ is chosen from:

linear and branched $C_1$-$C_{10}$ alkyl radicals optionally substituted by at least one entity chosen from OH and $OR_{19}$ groups, and radicals COOH, $CONH_2$, $CONHR_{11}$, and $CONR_{11}R_{12}$; and $R_2$ is chosen from:

linear and branched $C_1$-$C_6$ alkyl radicals, hydrogen atoms,

CN and $CF_3$ radicals; and $R_3$, $R_4$, $R_5$ and $R_6$, independently of one another, are chosen from:

aryl, heteroaryl and linear and branched $C_1$-$C_6$ alkyl radicals optionally interrupted by at least one entity chosen from groups $N(R_{13})$ and oxygen atoms, hydrogen atoms, radicals $OR_9$, halogens chosen from fluorine, chlorine and bromine, nitrogen-containing radicals chosen from $NH_2$, $NHR_7$ and $NR_7R_8$, COOH, CN and alkoxycarbonyl radicals $COOR_{10}$, where $R_7$, $R_8$, $R_9$ and $R_{10}$ are as defined above.

Synthesis Examples 4 and 5 are in accordance with this scheme.

Scheme II

When $R_2$ is chosen from COOH and alkoxycarbonyl radicals $COOR_{10}$, wherein $R_1$, $R_3$, $R_4$, $R_5$ and $R_6$ are as defined above, then a carboxylation step is added after the step of obtaining the indolizines 2b (Bobrovskii, S. I. et al., Mosk. Gos. Univ., Moscow, USSR. Khimiya Geterotsiklicheskikh Soedinenii 1989, (12), 1634-8):

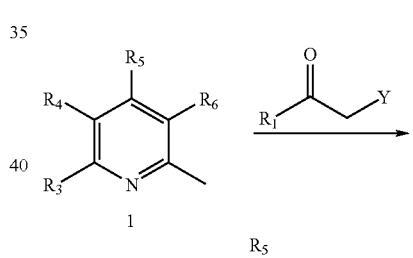

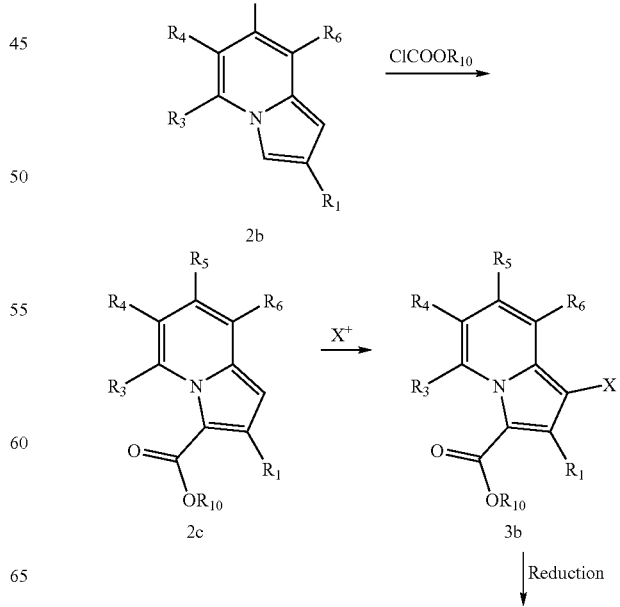

-continued

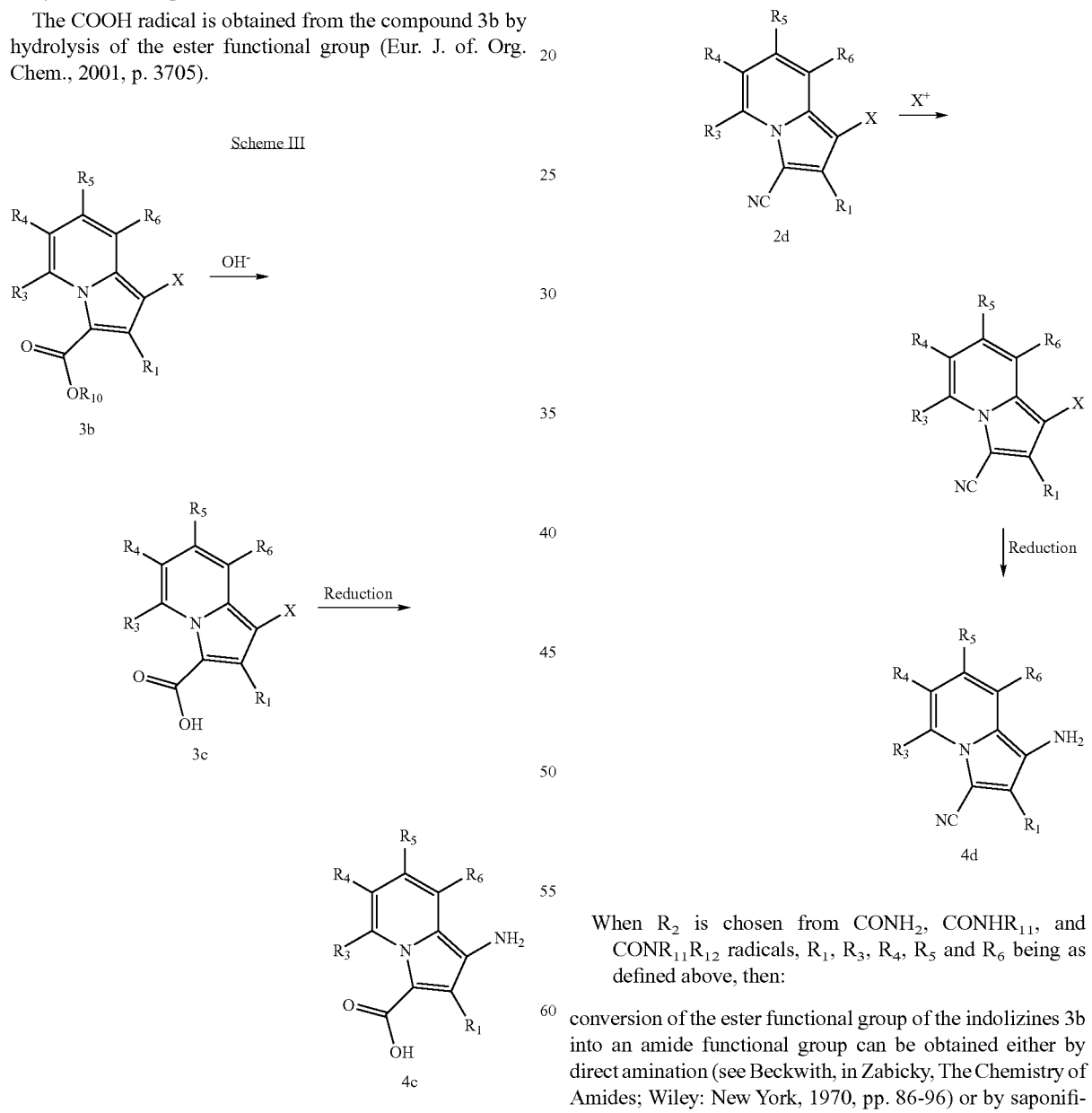

Synthesis Example 1 is in accordance with this scheme.

The COOH radical is obtained from the compound 3b by hydrolysis of the ester functional group (Eur. J. of. Org. Chem., 2001, p. 3705).

When $R_2$ is chosen from CN radicals, and $R_1$, $R_3$, $R_4$, $R_5$ and $R_6$ are as defined above, then the compound can be obtained directly from the compound 2b (Smaliy, R. V. et al., Synthesis, 2002, (16), p. 2416).

Scheme IV

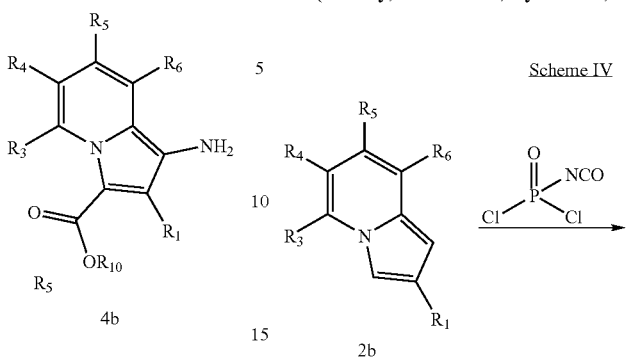

When $R_2$ is chosen from $CONH_2$, $CONHR_{11}$, and $CONR_{11}R_{12}$ radicals, $R_1$, $R_3$, $R_4$, $R_5$ and $R_6$ being as defined above, then:

conversion of the ester functional group of the indolizines 3b into an amide functional group can be obtained either by direct amination (see Beckwith, in Zabicky, The Chemistry of Amides; Wiley: New York, 1970, pp. 86-96) or by saponification of the ester functional group to carboxylic acid, followed by treatment with various amines (see Beckwith, in Zabicky, The Chemistry of Amides, pp. 105-109).

Scheme V
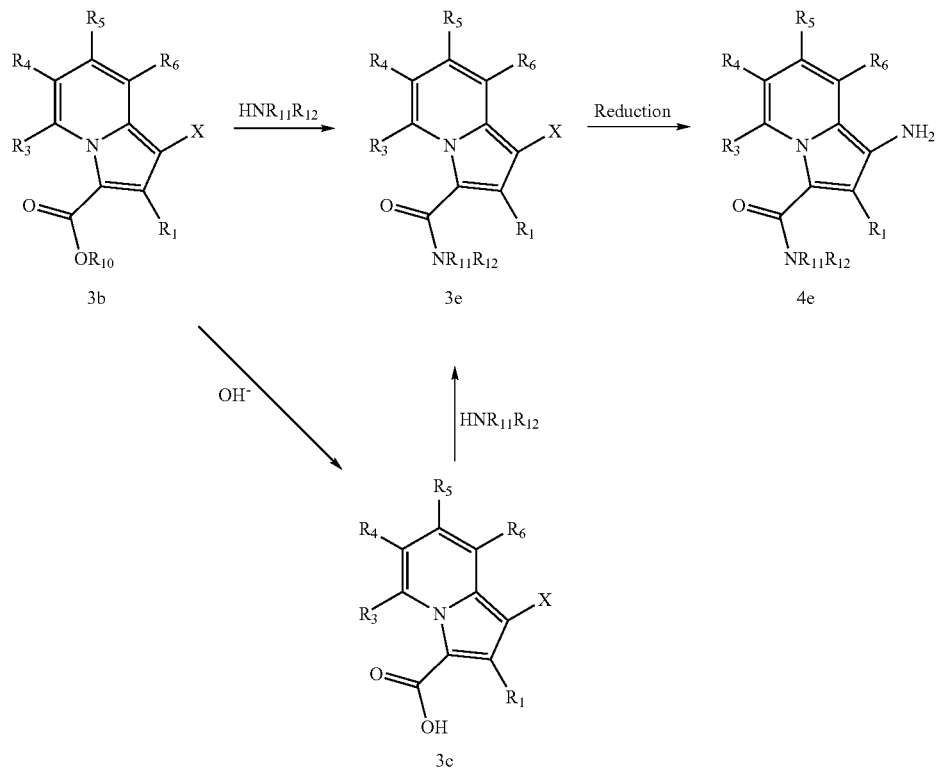
When $R_2$ is chosen from SR, SOR and $SO_2R$ radicals, $R_1$, $R_3$, $R_4$, $R_5$ and $R_6$ being as defined above, then:
there are a number of methods of introducing a group SR in position 3 of the indolizines of type 2b, for example:
  by reaction with a disulphide (Eur. Pat. Appl. 350384, 1990 and Synthesis, 1980, (11), pp. 886-7):
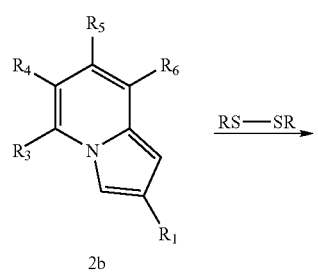
-continued
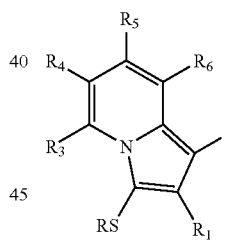
by reaction with a sulphur-containing derivative (Synthesis, 1980, (11), pp. 886-7):
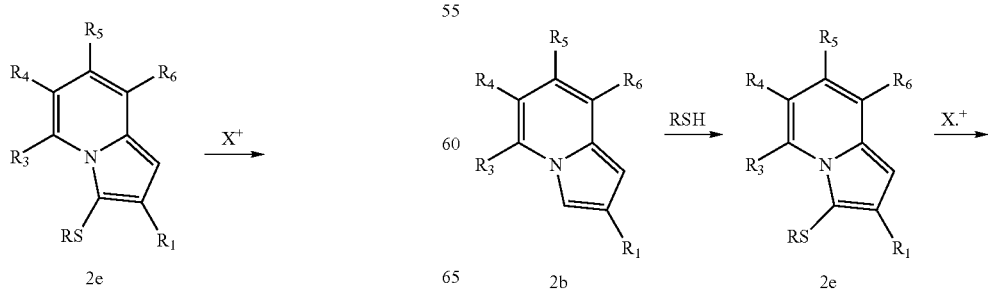

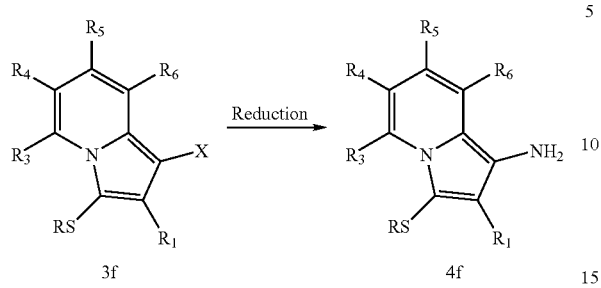

The conversion of a group SR to SOR or SO$_2$R at position 3 can be carried out from the indolizines of type 3f by oxidation, for example, of perbenzoic acids (Eur. Pat. Appl. 350384, 1990):

Scheme VI

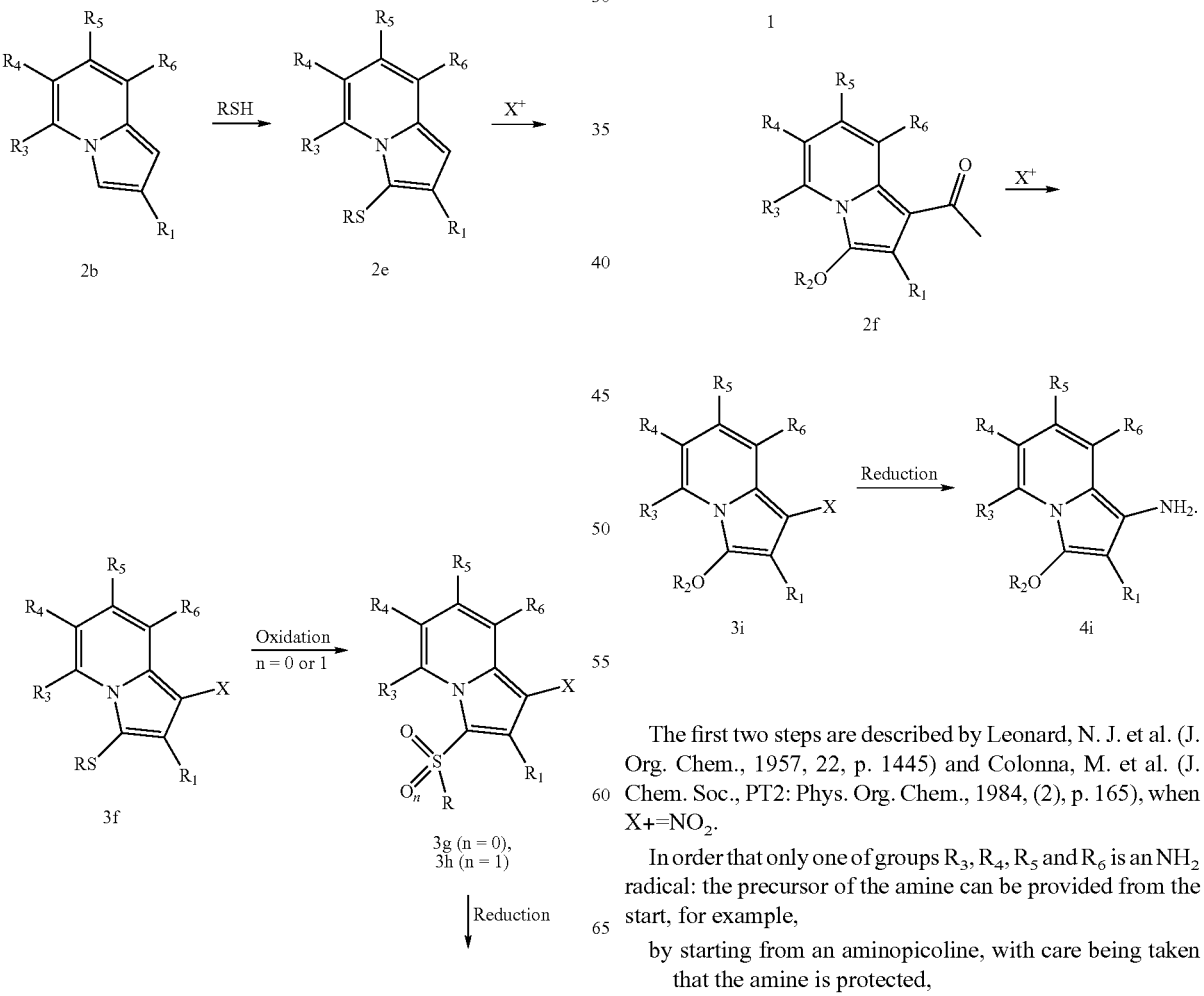

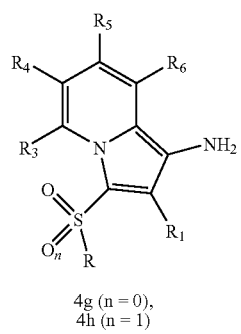

When R$_2$ is a radical OR$_9$, R$_1$, R$_3$, R$_4$, R$_5$ and R$_6$ being as defined above, then: it is possible to use the following procedure:

The first two steps are described by Leonard, N. J. et al. (J. Org. Chem., 1957, 22, p. 1445) and Colonna, M. et al. (J. Chem. Soc., PT2: Phys. Org. Chem., 1984, (2), p. 165), when X+=NO$_2$.

In order that only one of groups R$_3$, R$_4$, R$_5$ and R$_6$ is an NH$_2$ radical: the precursor of the amine can be provided from the start, for example, by starting from an aminopicoline, with care being taken that the amine is protected,

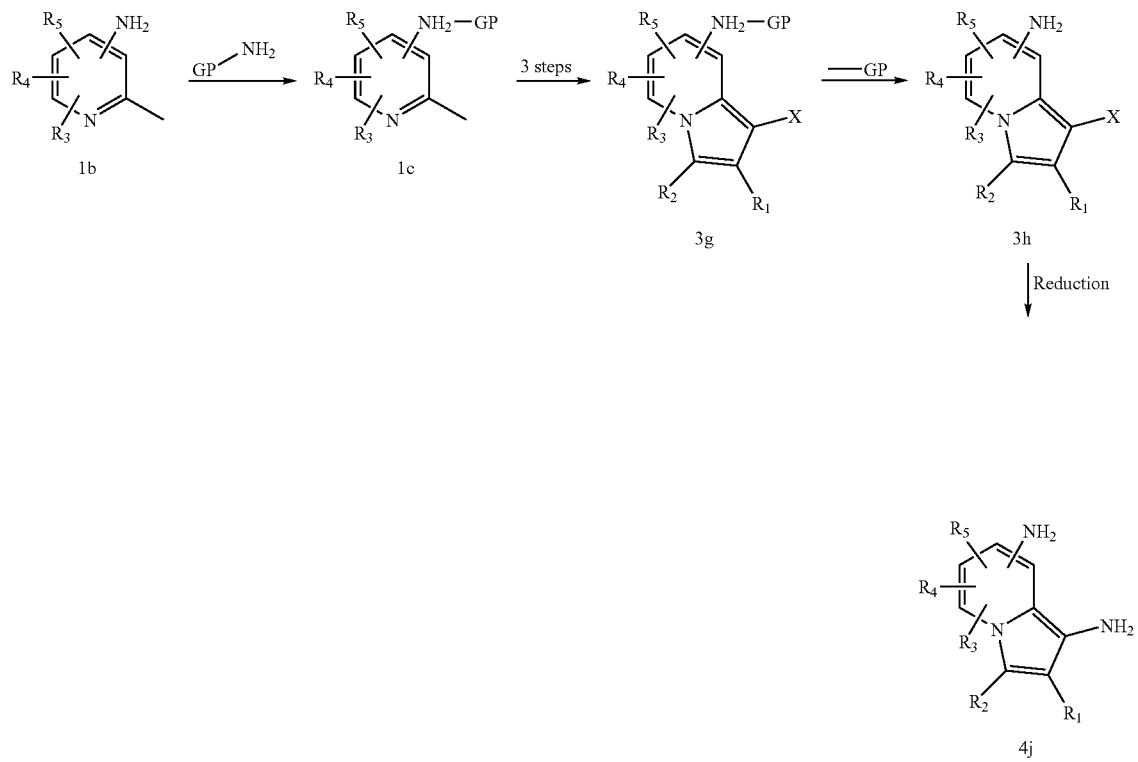

The deprotection step comes before the final reduction step. When the protecting group is a benzyl derivative, then the reduction by catalytic hydrogenation over Pd—C may serve as a deprotection step; or by introducing a halogen atom, which may subsequently lead to amine by substitution or by organometallic coupling

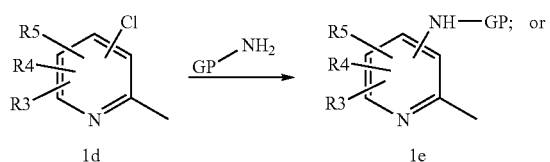

by starting from a nitropicoline, the amine being obtained during reduction.

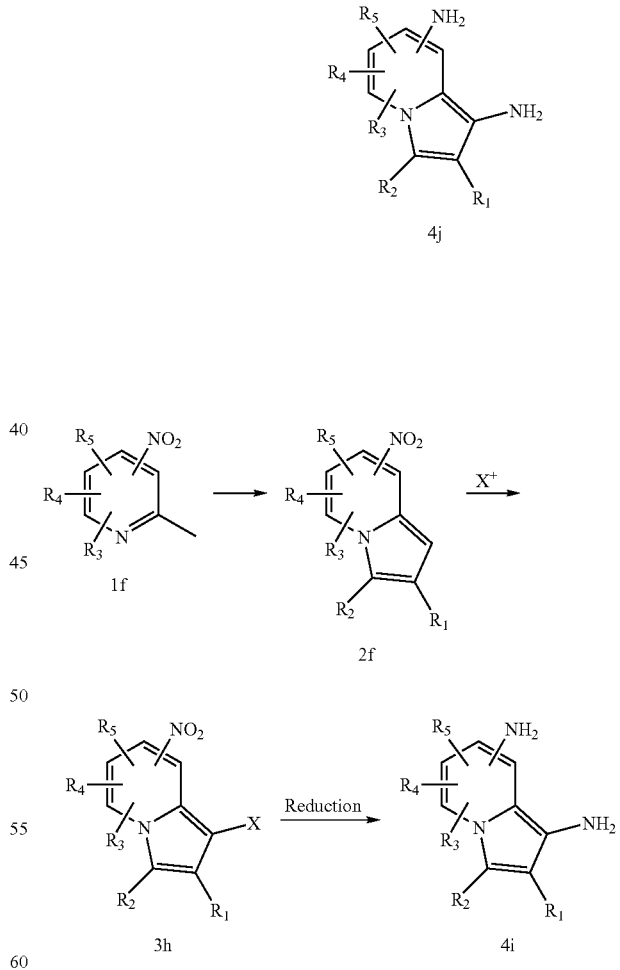

Method of Making the at Least One Aminoindolizine of Formula (I) Via Condensation of an Alkyl Alpha-haloacetate Derivative or Alpha-haloacetonitrile with a Pyridine, Followed by Cyclization by Reaction with a 2-Methylthionitroethene Derivative

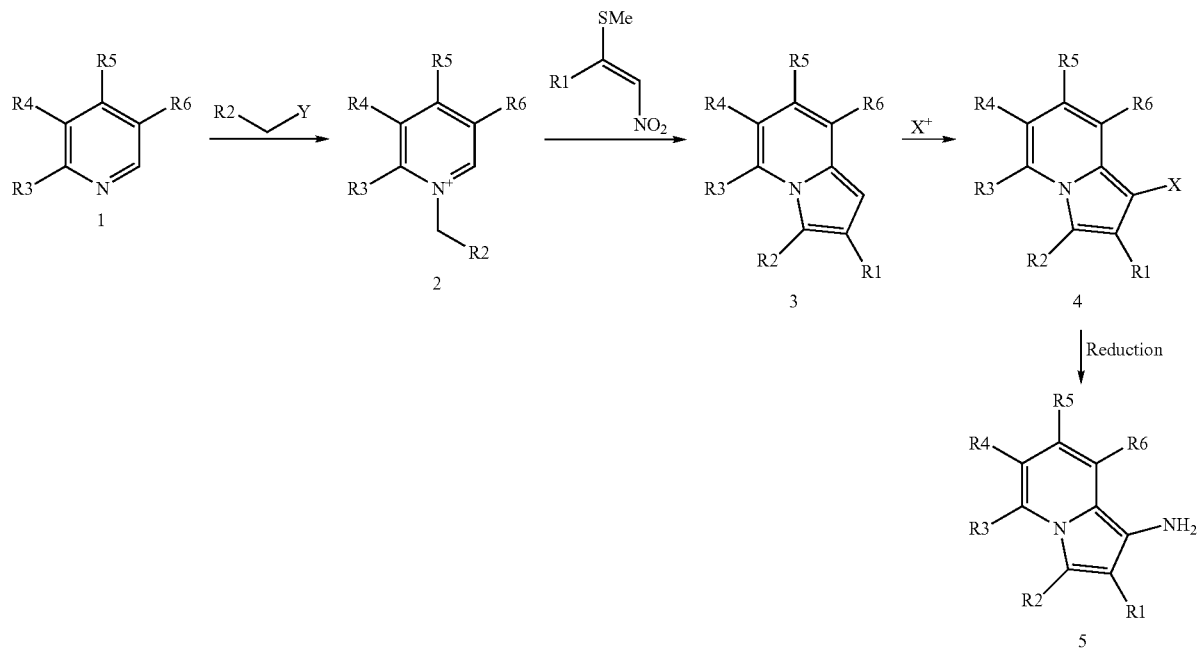

Wherein:
X is chosen from nitro, nitroso and azo (arylazo and heteroarylazo) radicals,
$R_1$ is chosen from:
linear and branched $C_1$-$C_{10}$ alkyl radicals,
sulphur-containing radicals chosen from SR, R being chosen from linear and branched $C_1$-$C_6$ alkyl radicals, and aryl radicals,
nitrogen-containing radicals chosen from $NHR_7$ and $NR_7R_8$,
$R_2$ is chosen from:
COOH and CN radicals and alkoxycarbonyl radicals $COOR_{10}$,
$R_3$, $R_4$, $R_5$ and $R_6$, independently from each other, are chosen from:
aryl, heteroaryl and linear and branched $C_1$-$C_6$ alkyl radicals optionally interrupted by at least one entity chosen from groups $N(R_{13})$ and oxygen,
hydrogen atoms,
radicals $OR_9$,
halogens chosen from fluorine, chlorine and bromine,
nitrogen-containing radicals chosen from $NH_2$ in a protected form, $NHR_7$ and $NR_7R_8$,
COOH and CN radicals and alkoxycarbonyl radicals $COOR_{10}$, where $R_7$, $R_8$, $R_9$ and $R_{10}$ are as defined above.

In this case the group $R_1$ may be introduced by at least 2 routes, including:
starting from bis-2-methylthionitroethene:

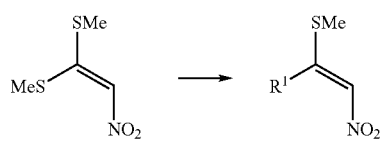

wherein $R_1$ can be chosen from:
linear and branched $C_1$-$C_{10}$ alkyl radicals, according to Teran, N. et al., Tetrahedron, 1998, 54(42), pp. 12973-84;
sulphur-containing radicals chosen from SR, in accordance with Rao, H. et al., Tet. Lett., 2003, 44(25), pp. 4701-4; and
nitrogen-containing radicals chosen from $NHR_7$ and $NR_7R_8$, in accordance with, for example, Wermuth, C. G. et al., J. Med. Chem., 1999, 42(4), 730-41; Ootsuka Y. et al., Jpn. Kokai Tokkyo Koho, 07157465, 1995 and Manjunatha, S. G. et al., Tet. Lett., 1990, 31(9), 1327-30.

After cyclization of the pyridinium 2 with bis-2-methylthionitroethene and oxidation of the sulphur-containing derivative 3a obtained, by substitution of sulphonyl group of 3b:

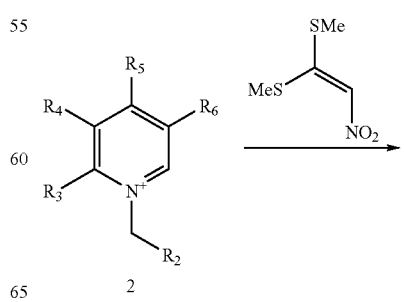

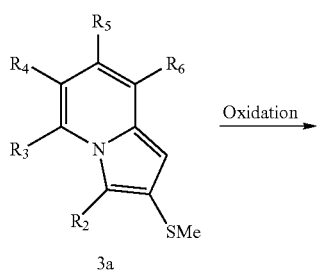

3a

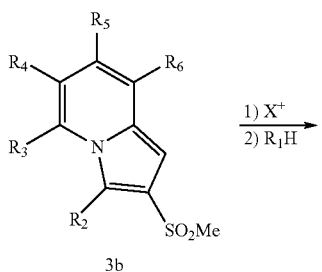

3b

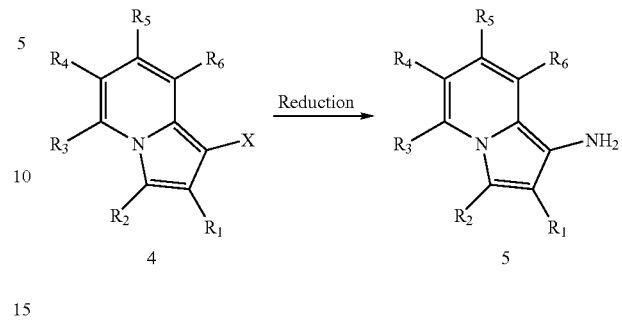

wherein $R_1$ can be chosen from:
- nitrogen-containing radicals chosen from $NH_2$, $NHR_7$ and $NR_7R_8$, and
- radicals $OR_9$.

With the proviso that if one of the groups $R_3$, $R_4$, $R_5$ and $R_6$ is an $NH_2$ radical, then $R_1$ must be other than H.

The precursor of the amine can be provided from the start, for example
- by starting from an aminopyridine, with the amine protected by a benzyl group (Andrews, A. F., J. Chem. Soc., PT1: Org. And Bio. Chem (1982), (12), 2995-3006 and Isin, E. M, JOC, (2001), 66(12), 4220-6)

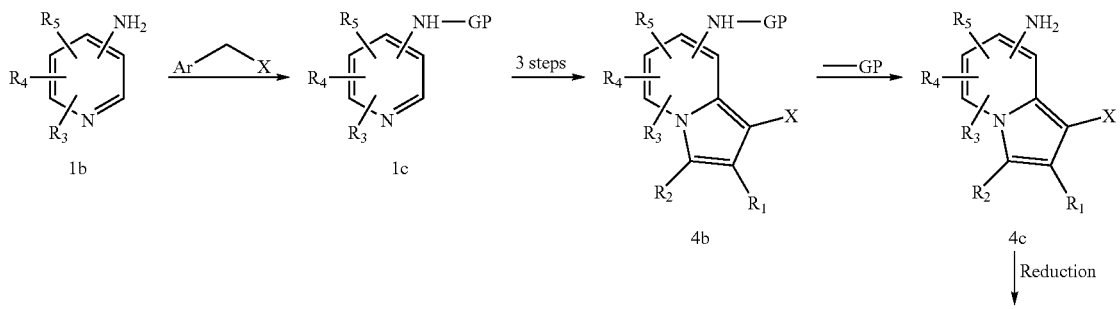

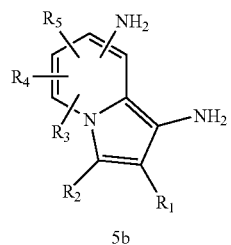

5b

The deprotection step should take place before the final reduction step. Where the protecting group is a benzyl derivative, the reduction, by catalytic hydrogenation over Pd—C, may serve as a deprotection step.

by starting from a halogen atom, wherein the amino group can be introduced by substitution (Shimizu, K. et al., Jpn Kokai Tokkyo Koho (2001) JP 2001151753) or by organometallic coupling (Desmarets, C. et al., JOC, (2002), 67(9), 3029-36).

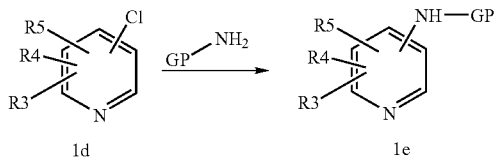

by starting from a nitropyridine, wherein the amine is obtained in the reduction step.

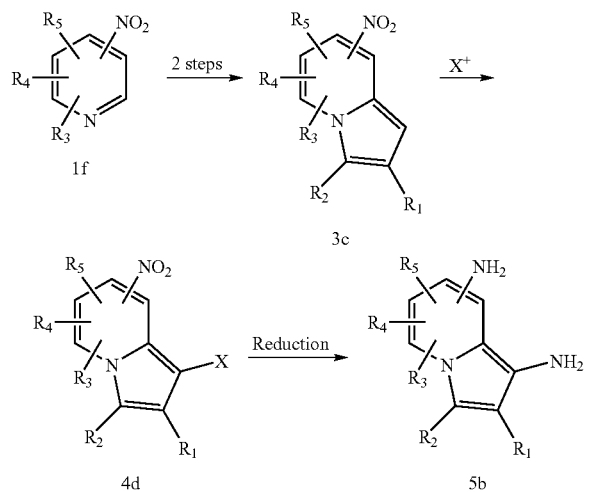

Also disclosed herein are the aminoindolizines of formula (II):

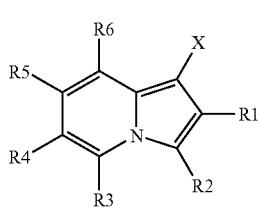

wherein:
X is chosen from
nitro, nitroso, arylazo and heteroarylazo radicals,
radicals NHCOR$_{15}$, R$_{15}$ being chosen from linear and branched C$_1$-C$_6$ alkyl, and aryl and heteroaryl radicals,
R$_1$ is a radical chosen from:
linear and branched C$_1$-C$_{10}$ alkyl radicals optionally substituted by at least one group chosen from OH and OR$_{19}$ groups, R$_{19}$ being chosen from linear and branched C$_1$-C$_6$ alkyl radicals optionally substituted by at least one OH radical,
sulphur-containing radicals chosen from SR and SO$_2$Me, R being chosen from linear and branched C$_1$-C$_6$ alkyl radicals and aryl radicals,
nitrogen-containing radicals chosen from NH$_2$, NHR$_7$ and NR$_7$R$_8$, wherein R$_7$ and R$_8$, which are identical or different, are chosen from linear and branched C$_1$-C$_6$ alkyl radicals optionally substituted by at least one group chosen from hydroxyl, amino, C$_1$-C$_6$ mono- and dialkylamino, carboxamido, ureido and guanidinyl groups, and optionally interrupted by at least one group chosen from N(R$_{13}$) and oxygen, R$_{13}$ being chosen from a hydrogen atom and C$_1$-C$_6$ alkyl radicals, it being possible for the radicals R$_7$ and R$_8$ to form, together with the nitrogen atom to which they are attached, a saturated or unsaturated heterocycle containing 5 to 7 ring members,
the radicals OR$_9$, R$_9$ being chosen from linear and branched C$_1$-C$_6$ alkyl radicals optionally substituted by at least one OH radical, and from linear and branched C$_1$-C$_6$ alkoxy radicals,
radicals chosen from COOH, CONH$_2$, CONHR$_{11}$ and CONR$_{11}$R$_{12}$, wherein R$_{11}$ and R$_{12}$, which are identical or different, are chosen from linear and branched C$_1$-C$_6$ alkyl radicals optionally interrupted by at least one group N(R$_{14}$), R$_{14}$ being chosen from a hydrogen atom and C$_1$-C$_6$ alkyl radicals optionally substituted by a hydroxyl group; it being possible for the radicals R$_{11}$ and R$_{12}$ to form, together and with the nitrogen atom to which they are attached, a saturated or unsaturated heterocycle containing 5 to 7 ring members,
R$_2$ is a radical chosen from:
linear and branched C$_1$-C$_6$ alkyl radicals,
hydrogen atoms,
radicals chosen from COOH, CN, CF$_3$ and alkoxycarbonyl COOR$_{10}$, R$_{10}$ being chosen from linear and branched C$_1$-C$_6$ alkyl radicals, and aryl and heteroaryl radicals,
radicals chosen from CONH$_2$, CONHR$_{11}$ and CONR$_{11}$R$_{12}$,
the radicals OR$_9$, and
radicals SR, SOR, and SO$_2$R,
where R, R$_9$, R$_{11}$ and R$_{12}$ are as defined above,
R$_3$, R$_4$, R$_5$ and R$_6$, independently of one another, are chosen from:
aryl, heteroaryl, linear and branched C$_1$-C$_6$ alkyl radicals optionally interrupted by at least one group chosen from N(R$_{13}$) groups and oxygen,
the radicals OR$_9$, with R$_9$ being chosen from C$_1$-C$_4$ alkyl radicals, such as —OCH$_3$,
hydrogen atoms,
halogens chosen from fluorine, chlorine and bromine,
nitrogen-containing radicals chosen from NH$_2$, NHR$_7$ and NR$_7$R$_8$,
COOH and CN radicals and alkoxycarbonyl radicals COOR$_{10}$,
where R$_7$, R$_8$, R$_9$, R$_{10}$ and R$_{13}$ are as defined above,
with the proviso that not more than one of the radicals R$_1$, R$_3$, R$_4$, R$_5$ and R$_6$ is a nitrogen-containing radical chosen from NH$_2$, NHR$_7$ and NR$_7$R$_8$, with the exception of the compounds:

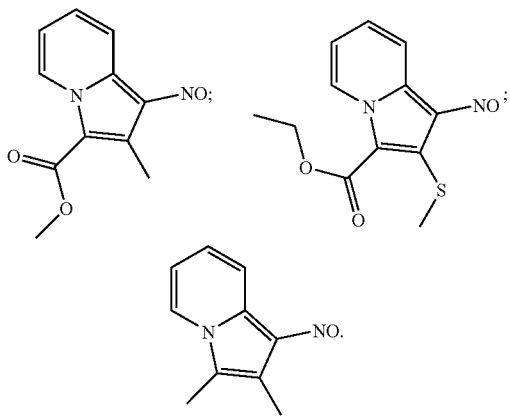

Also disclosed herein are the uses of at least one aminoindolizine of formula (I) and the salts and solvates thereof in processes for dyeing keratin fibers, including human keratin fibers such as the hair.

Further disclosed herein is a cosmetic dyeing composition, for example, for keratin fibers such as the hair, comprising, in a medium appropriate for dyeing, at least one chemical entity chosen from aminoindolizines of formula (I), acid addition salts thereof, and solvates thereof.

For example, the at least one chemical entity can be present in an amount ranging from 0.0001% to 20%, for example, from 0.005% to 6% by weight, relative to the total weight of the composition.

The medium appropriate for dyeing generally may comprise water or a mixture of water and at least one organic solvent for example, chosen from, branched and unbranched $C_1$-$C_4$ lower alcohols, such as ethanol and isopropanol; polyols and polyol ethers such as 2-butoxyethanol, propylene glycol, propylene glycol monomethyl ether, diethylene glycol monoethyl ether and monomethyl ether; glycerol; and aromatic alcohols such as benzyl alcohol and phenoxyethanol.

The cosmetic composition may further comprise at least one cosmetic adjuvant chosen from antioxidants, penetrants, sequestrants, fragrances, buffers, dispersants, surfactants, conditioning agents, film formers, polymers, ceramides, preservatives, pearlizing and opacifying agents, vitamins and provitamins.

The above adjuvants may be present in an amount, for each of them, ranging from 0.01% to 20% by weight, relative to the weight of the composition.

The composition according to the present disclosure may also comprise at least one oxidation coupler.

These oxidation couplers are chosen from meta-phenylenediamines, meta-aminophenols, meta-diphenols, naphthalenic couplers and heterocyclic couplers, and the addition salts thereof.

Examples include but are not limited to 2-methyl-5-aminophenol, 5-N-(β-hydroxyethyl)amino-2-methylphenol, 6-chloro-2-methyl-5-aminophenol, 3-aminophenol, 1,3-dihydroxybenzene (resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene and the addition salts thereof.

The at least one oxidation coupler may be present in a total amount ranging from 0.0001% to 20%, for example, from 0.005% to 6% by weight, relative to the total weight of the composition.

The composition may further comprise at least one additional oxidation base other than the at least one aminoindolizine of formula (I). These bases may, for example, be chosen from para-phenylenediamines, bis-phenylalkylenediamines, para-aminophenols, ortho-aminophenols, heterocyclic bases, and the addition salts thereof.

The para-phenylenediamines include, by way of non-limiting example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol and the acid addition salts thereof.

Among the abovementioned para-phenylenediamines, further mention may be made of para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

The bisphenylalkylenediamines include, by way of non-limiting example, N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

The para-aminophenols include, by way of non-limiting example, para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino- 2-methylphenol, 4-amino-2-hydroxymethylphenol, 4-amino-2-methoxymethyl phenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'amino-2'hydroxy-3'-methyl)phenyl)methyl]-2-methylphenol, bis[(5'amino-2'hydroxy)phenyl]methane, and the acid addition salts thereof.

The ortho-aminophenols include, by way of non-limiting example, 2-aminophenol, 2-amino-5-methylphenol, 2-amino-6-methylphenol, 5-acetamido-2-aminophenol, and the acid addition salts thereof.

Among the heterocyclic bases, examples include but are not limited to pyridine derivatives, pyrimidine derivatives, and pyrazole derivatives.

The pyridine derivatives include but are not limited to the compounds described, for example, in British Patent Nos. GB 1 026 978 and GB 1 153 196, such as 2,5-diaminopyridine, 2-(4-methoxyphenyl)amino-3-aminopyridine, 3,4-diaminopyridine, and the acid addition salts thereof.

Other pyridine oxidation bases that may be used in the present disclosure include, by way of non-limiting example, the 3-aminopyrazolo[1,5-a]pyridine oxidation bases and/or their addition salts, described, for example, in French Patent Application Publication No. FR 2 801 308. Examples include but are not limited to pyrazolo[1,5-a]pyridin-3-ylamine; 2-acetylaminopyrazolo-[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazole[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)(2-hydroxyethyl)amino]ethanol; 2-[(3-aminopyrazolo[1,5-a]pyridin-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and the acid addition salts thereof.

The pyrimidine derivatives include but are not limited to the compounds described, for example, in German Patent No. DE 23 59 399; Japanese Publication Nos. JP 88-169571 and JP 05-63124; European Patent No. EP 07 70 375 or PCT Application Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

The pyrazole derivatives include but are not limited to the compounds described in the German Patent Nos. DE 3843892, DE 4133957, and DE 195 43 988, and PCT Application Publication Nos. WO 94/08969 and WO 94/08970, French Publication No. FR-A-2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

The at least one additional oxidation base other than the aminoindolizines of formula (I) may be present in an amount ranging from 0.0001% to 20%, for example, from 0.005% to 6%, by weight, relative to the total weight of the composition.

Generally speaking, the addition salts with an acid that can be used for the oxidation bases and the couplers are chosen from hydrochlorides, hydrobromides, sulphates, citrates, succinates, tartrates, lactates, tosylates, benzenesulphonates, phosphates and acetates.

The dyeing composition in accordance with the present disclosure may further comprise at least one direct dyes, which, for example, may be chosen from neutral, acidic, and cationic nitro dyes of the benzene series; neutral, acidic, and cationic direct azo dyes; neutral, acidic, and cationic direct quinone, and such as anthraquinone, dyes; direct azine dyes, direct methine, azomethine, triarylmethane and indoamine dyes; and direct natural dyes. The composition according to the present disclosure may, for example comprise at least one dye chosen from cationic direct dyes and natural direct dyes.

The cationic direct dyes which can be used according to the present disclosure include, for example, the cationic direct azo dyes described in PCT Patent Application Publication Nos. WO 95/15144 and WO-95/01772, and European Application Publication No. EP-714954.

These compounds include the following dyes, which are mentioned in a non-limiting manner:

1,3-dimethyl-2-[[4-(dimethylamino)phenyl]azo]-1H-imidazolium chloride, 1,3-dimethyl-2-[(4-aminophenyl)azo]-1H-imidazolium chloride, and 1-methyl-4-[(methylphenylhydrazono)methyl]pyridinium methyl sulphate.

The direct natural dyes which can be used according to the present disclosure include, by way of non-limiting example, lawsone, juglone, alizarin, purpurin, carminic acid, kermesic acid, purpurogallin, protocatechaldehyde, indigo, isatin, curcumin, spinulosin and apigenidin. It is also possible to use the extracts or decoctions containing these natural dyes, for example, the cataplasms and henna-based extracts.

The amount of the at least one direct dye may range for example, from 0.001% to 20% by weight, relative to the total weight of the composition, and for example, may range from 0.005% to 10% by weight.

The person skilled in the art would of course ensure that the at least one adjuvant, additional oxidation dye precursors and direct dyes are chosen such that the beneficial properties intrinsically attached to the oxidation dyeing composition in accordance with the present disclosure are not, or are not substantially, adversely affected by the intended addition or additions.

The pH of the dyeing composition in accordance with the present disclosure may range from 3 to 12, for example, from 5 to 11. It may be adjusted to the desired value via acidifying or alkalifying agents which are known to a skilled artisan in the dyeing of keratin fibers or else using conventional buffer systems.

The acidifying agents include, by way of non-limiting example, organic and inorganic acids other than carboxylic diacids, such as hydrochloric acid, ortho-phosphoric acid, sulphuric acid, carboxylic acids such as acetic acid, tartaric acid, citric acid, lactic acid, and sulphonic acids.

The alkalifying agents include, by way of non-limiting example, ammonia, alkali metal carbonates, alkanolamines such as mono-, di- and triethanolamines and their derivatives, sodium hydroxide or potassium hydroxide, and the compounds of formula:

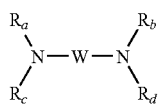

wherein W is a propylene residue optionally substituted by a hydroxyl group or a $C_1$-$C_4$ alkyl radical, and $R_a$, $R_b$, $R_c$ and $R_d$, which are identical or different, are chosen from a hydrogen atom, $C_1$-$C_4$ alkyl, and $C_1$-$C_4$ hydroxyalkyl radicals.

The cosmetic composition according to the present disclosure may be present in a variety of forms, such as in the form of liquids, creams, gels, or any other form which is appropriate for carrying out dyeing of keratin fibers, such as human hair.

Further disclosed herein is a method of dyeing keratin fibers wherein the composition according to the present disclosure, as defined above, is applied to the keratin fibers for a time sufficient to develop the desired coloration in the presence of an oxidizing agent, the oxidizing agent being applied before, simultaneously with or after the composition.

The color may be revealed at acidic, neutral or alkaline pH and the at least one oxidizing agent may be added to the composition of the present disclosure at the time of use, or may be employed from an oxidizing composition containing it, wherein this oxidizing composition can be applied simultaneously with or sequentially to the composition of the present disclosure.

In at least one embodiment, the composition according to the present disclosure is mixed, for example, at the time of use, into a composition comprising, in a medium appropriate for dyeing, at least one oxidizing agent, the at least one oxidizing agent being present in an amount sufficient to develop a coloration.

In at least one embodiment, a ready-to-use composition is available, which is a mixture of at least one composition according to the present disclosure with at least one oxidizing agent. The resulting mixture is applied to the keratin fibers for a time sufficient for the desired coloration to develop. After a waiting time ranging from 3 to 50 minutes, such as from 5 to 30 minutes, the keratin fibers are rinsed, washed with shampoo, rinsed again and then dried.

The oxidizing agents that may be used for the oxidation dyeing of keratin fibers include, for example, hydrogen peroxide, urea peroxide, alkali metal bromates, persalts such as perborates and persulphates, peracids and oxidase enzymes, including without being limited to peroxydases, 2-electron oxidoreductases, such as uricases, and 4-electron oxygenases, such as laccases. In at least one embodiment, the at least one oxidizing agent is hydrogen peroxide.

The oxidizing composition may further comprise at least one adjuvant conventionally in compositions for dyeing hair, as defined above.

The pH of the oxidizing composition comprising the at least one oxidizing agent is such that, after it has been mixed with the dyeing composition, the pH of the resulting composition applied to the keratin fibers ranges, for example, from 3 to 12, and further ranges from 5 to 11. It may be adjusted to the desired value via acidifying or alkalifying agents which are commonly used in the dyeing of keratin fibers, as defined above.

The ready-to-use composition which is ultimately applied to the keratin fibers may be present in a variety of forms, such as in the form of liquids, creams or gels or any other form appropriate for carrying out dyeing of keratin fibers, such as human hair.

Further disclosed herein is a method of dyeing keratin fibers, wherein the ready-to-use composition is applied to said fibers for a time sufficient to develop the desired coloration.

The time sufficient for the desired coloration to develop can range from 3 to 50 minutes, such as from 5 to 30 minutes.

Further disclosed herein is a multi-compartment device or kit for dyeing, wherein at least one first compartment contains the at least one above-defined dyeing composition and at least one second compartment contains at least one oxidizing composition. This device may be equipped with an applicator that allows the desired mixture to be delivered to the hair, such as the devices described in French Patent No. FR-2 586 913t.

Using this device, it is possible to dye the keratin fibers from a method comprising mixing at least one dyeing composition in accordance with the present disclosure with at least one oxidizing agent as defined above, and applying the resulting mixture to the keratin fibers for a time sufficient for the desired coloration to develop.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following examples are intended to illustrate the present disclosure without, however, being limiting in nature.

EXAMPLES

Synthesis Examples

Example 1

Synthesis of Methyl 2-methyl-1-aminoindolizine-3-carboxylate (4) (Compound B)

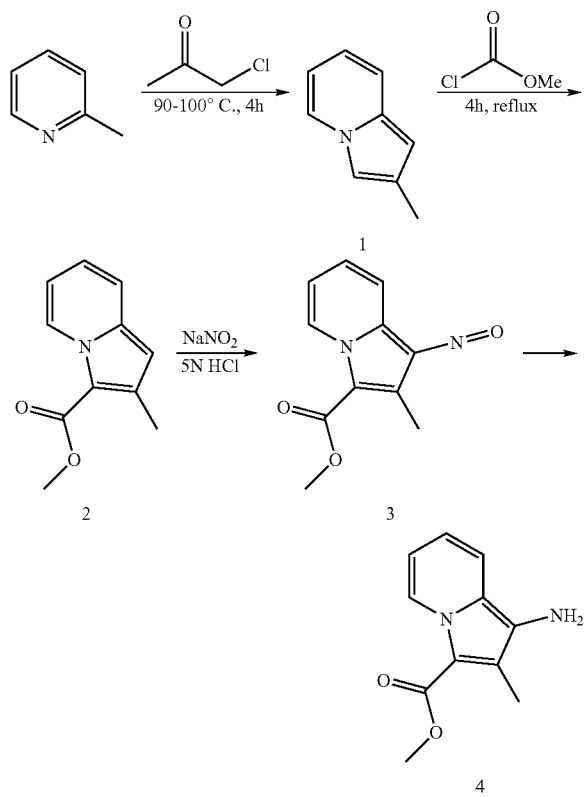

Preparation of 2-methylindolizine (1). A mixture of α-picoline (5 g, 53.8 mmol) and chloroacetone (5 g, 53.8 mmol) was heated at 90-100° C. for 4 h. The reaction mixture was then poured into a chloroform/water mixture (50:50 mL) and subsequently extracted. The aqueous phase was treated with 0.6 g of sodium bicarbonate and then extracted with diethyl ether (3×30 mL) to remove the residual α-picoline. A further 8.1 g (96.4 mmol) of sodium bicarbonate were added to the aqueous phase, and the mixture was concentrated to give a mixture of white precipitate and water. Extracting the mixture with diethyl ether gave 5.6 g of 2-methylindolizine 1 in the form of white crystals; m.p.: 57-58° C. $^1$H NMR (CDCl$_3$): δ 7.77-7.74 (m, 1H), 7.23 (d, J=8.9 Hz, 1H), 7.06 (s, 1H), 6.58-6.53 (m, 1H), 6.36-6.31 (m, 1H), 6.21 (s, 1H), 2.31 (s, 3H), $^{13}$C NMR (CDCl$_3$): δ 132.8, 124.8, 124.6, 118.2, 116.5, 111.1, 109.4, 99.7, 12.4.

Preparation of methyl 2-methylindolizine-3-carboxylate (2). A mixture of 2-methylindolizine 1 (3.8 g, 29.0 mmol) and methyl chloroformate (22 g (18 ml), 231.6 mmol) was heated at reflux for 2 h. A further 12.2 g (10 ml) of methyl chloroformate were added, and the mixture was heated at reflux for 2 h. The reaction mixture was concentrated under vacuum and then purified by chromatography on a silica column (hexane/ethyl acetate 5:1, silica gel 200-425 mesh) to give 4 g of compound 2 (colorless oil). $^1$H NMR (CDCl$_3$): δ 9.43 (d, J=7.1 Hz, 1H), 7.35 (d, J=8.8 Hz, 1H), 6.99-6.93 (m, 1H), 6.73-6.68 (m, 1H), 6.29 (s, 1H), 3.91 (s, 3H), 2.53 (s, 3H), $^{13}$C NMR (CDCl$_3$): δ 162.7, 137.0, 134.6, 127.6, 121.8, 117.6, 111.8, 103.5, 103.48, 50.6, 15.1.

Preparation of methyl 2-methyl-1-nitrosoindolizine-3-carboxylate (3). A solution of sodium nitrite (2.2 g, 31.90 mmol) in water (10 mL) was added slowly at 0-5° C. to a stirred solution of methyl 2-methylindolizine-3-carboxylate 2 (3.9 g, 20.61 mmol) in glacial acetic acid (50 mL). After 30 min, the brown reaction mixture was poured into water. Green crystals were collected by filtration, washed with water and then dried under vacuum to give 3.7 g of expected compound; m.p.: 131-132° C. $^1$H NMR (CDCl$_3$): 9.63 (d, J=7.0 Hz, 1H), 8.39 (d, J=8.5 Hz, 1H), 7.74-7.69 (m, 1H), 7.23-7.18 (m, 1H), 4.03 (s, 3H), 3.26 (s, 3H), $^{13}$C NMR (CDCl$_3$): δ 162.5, 154.5, 141.7, 135.7, 127.9, 123.2, 118.4, 118.3, 114.5, 51.7, 11.1. Analysis calculated for $C_{11}H_{10}N_2O_3$: C, 60.55; H, 5.54; N, 12.84, found: C, 60.65; H, 5.60; N, 12.90.

Preparation of methyl 2-methyl-1-aminoindolizine-3-carboxylate (4). A 250 mL three-necked flask equipped with a magnetic stirrer, a thermometer and a condenser was charged in succession with 96 mL of ethanol, 5 mL of water and 4 g of zinc powder. The reaction mixture was heated to reflux and a solution of 260 mg of ammonium chloride in 2 ml of water was run in. Subsequently, in small portions, using a spatula, 1.09 g (5 mmol) of methyl 2-methyl-1-nitrosoindolizine-3-carboxylate were introduced over 30 minutes.

Reflux was maintained for an hour:

The zinc salts were removed by filtration over Celite. The filtrates were acidified by means of a hydrochloric isopropanol solution and then concentrated under vacuum.

The pasty solid thus obtained was taken up in a minimum amount of methanol and precipitated from diisopropyl ether.

The beige white solid formed was filtered with suction on a No. 4 frit and then dried under vacuum in the presence of P$_2$O$_5$. After drying, a mass of 0.8 g of expected product was recovered.

The mass-spectrometry and NMR-spectroscopy analyses were in accordance with the expected structure:

the main ions detected were the quasi-molecular ions (MH)+ and (MNa)+ of the expected molecule, $C_{11}H_{12}N_2O_2$.

$^1$H NMR (DMSO-d6): δ 3.86 (s, 3H), 7.02 (unresolved complex, 1H), 7.28 (m, 1H), 7.92 (m, 1H), 9.37 (m, 1H), 10.3 (bs, 3H).

Example 2

Synthesis of Ethyl 2-methylamino-1-aminoindolizine-3-carboxylate (8) (Compound AB)

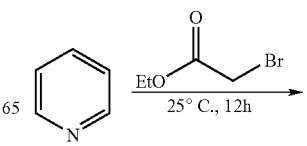

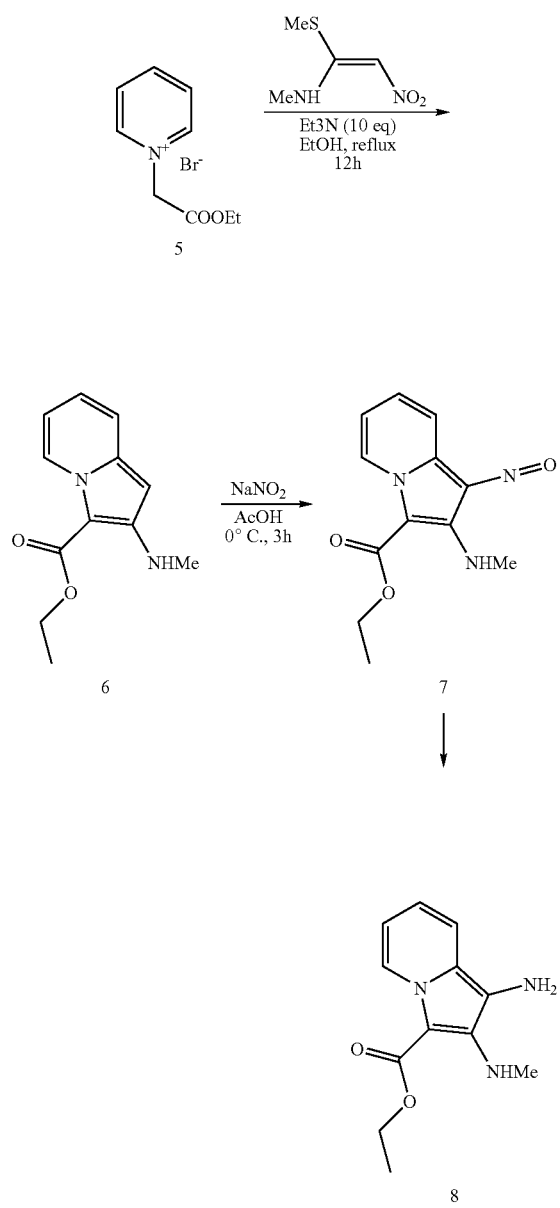

Preparation of 1-ethoxycarbonylmethylpyridinium bromide (5) [2003, J. Med. Chem, p. 4872]

A mixture of pyridine (3 g, 38 mmol) and ethyl bromoacetate (6.3 g, 38 mmol) in 30 ml of ethyl acetate was stirred for 12 h. The precipitate formed was isolated by filtration and washed with diethyl ether (30 ml), to give, after drying, 7 g of 1-ethoxycarbonylmethylpyridinium bromide 5.

Preparation of Ethyl 2-methylaminoindolizine-3-carboxylate (6).

A mixture of 1-ethoxycarbonylmethylpyridinium bromide 5 (1 g, 4.1 mmol), 1,1-bismethylthio-2-nitroethene (1.2 g; 8.1 mmol) and $Et_3N$ (4.1 g, 40.6 mmol) in ethanol (30 mL) was heated at reflux for 12 h. The solvents and the triethylamine were then evaporated under vacuum. The oil obtained was extracted with water (50 mL) and toluene (3×50 mL). The combined extracts were dried over anhydrous magnesium sulphate, filtered and then concentrated under vacuum. The residue was chromatographed on a column of silica with an elution gradient of 1/1 to 4/1 of ethyl acetate/petroleum ether. This gave 0.5 g of ethyl 2-methylaminoindolizine-3-carboxylate 6 in the form of an oil. $^1$H NMR (DMSO-$d_6$) δ: 9.11 (br s, 1H), 7.32 (d, J=8.8 Hz, 1H), 7.07-7.01 (m, 1H), 6.71-6.66 (m, 1H), 5.88 (br s, 1H), 5.85 (s, 1H), 4.32 (q, J=7.0 Hz, 2H), 2.85 (d, J=5.1 Hz, 3H), 1.34 (t, J=7.0 Hz, 1H), $^{13}$C NMR (CDCl$_3$) δ: 161.0, 148.9, 138.2, 127.0, 123.4, 115.8, 109.9, 98.6, 84.3, 58.7, 31.0, 14.7.

Preparation of Ethyl 2-methylamino-1-nitrosoindolizine-3-carboxylate (7).

Ethyl 2-(methylamino)-3-indolizinecarboxylate 6 (4.45 g, 20.4 mmol) was dissolved in CH$_3$COOH (40 mL) and cooled to 0° C., before a solution of sodium nitrite (1.7 g, 24.0 mmol) in water (10 mL) was added. After being stirred at 0° C. for 3 h, the reaction mixture was basified with a 2 M solution of NaOH (pH=8-9) and extracted with CH$_2$Cl$_2$ (3×50 mL). The combined extracts were dried over anhydrous magnesium sulphate, filtered and then concentrated under vacuum. The residue was chromatographed on silica gel with an elution gradient of 1/1 to 4/1 of ethyl acetate/petroleum ether, to give, following removal of the solvents, 3.89 g of green microcrystals of ethyl 2-(methylamino)-1-nitroso-3-indolizinecarboxylate 7, m.p.: 156-157° C. $^1$H NMR (DMSO-$d_6$): δ 1.40 (t, J=7.0 Hz, 3H), 3.47 (d, J=5.4 Hz, 3H), 4.38 (q, J=7.0 Hz, 2H), 7.35 (t, J=7.0 Hz, 1H), 7.23 (t, J=8.1 Hz, 1H), 7.79 (br s, 1H), 8.38 (d, J=8.1 Hz, 1H), 9.27 (br s, 1H). $^{13}$C NMR (DMSO-$d_6$): δ 14.5, 34.5, 59.7, 98.8, 116.2, 120.0, 123.5, 128.1, 135.2, 149.4, 149.8, 160.9.

Preparation of Ethyl 2-methylamino-1-aminoindolizine-3-carboxylate (8).

A 250 mL three-necked flask equipped with a magnetic stirrer, a thermometer and a condenser was charged in succession with 150 mL of ethanol, 1.5 mL of water and 5 g of zinc powder. The mixture was heated to reflux and a solution of 100 mg of ammonium chloride in 1.5 ml of water was run in. Then, in small portions, using a spatula, 0.5 g (2.02 mmol) of ethyl 2-methylamino-1-nitrosoindolizine-3-carboxylate was introduced over 20 minutes. At the end of the addition, 2 ml of acetic acid were added and the reflux was maintained for an hour.

The zinc salts were removed by filtration over Celite. The filtrates were acidified using a hydrochloric isopropanol solution and then concentrated under vacuum.

The pasty solid thus obtained was taken up in a minimum amount of methanol and precipitated from diisopropyl ether.

The beige white solid formed was filtered with suction on a No. 4 frit and then dried under vacuum in the presence of P$_2$O$_5$. After drying, a mass of 0.4 g of expected product was recovered.

The mass-spectrometry and NMR-spectroscopy analyses were in accordance:

the main ions detected were the quasi-molecular ions (MH)+, (MNa)+ of the expected molecule, C$_{12}$H$_{15}$N$_3$O$_2$.

Example 3

Synthesis of Ethyl 2-(methylsulphonyl)-1-amino-3-indolizinecarboxylate (12) (Compound D)

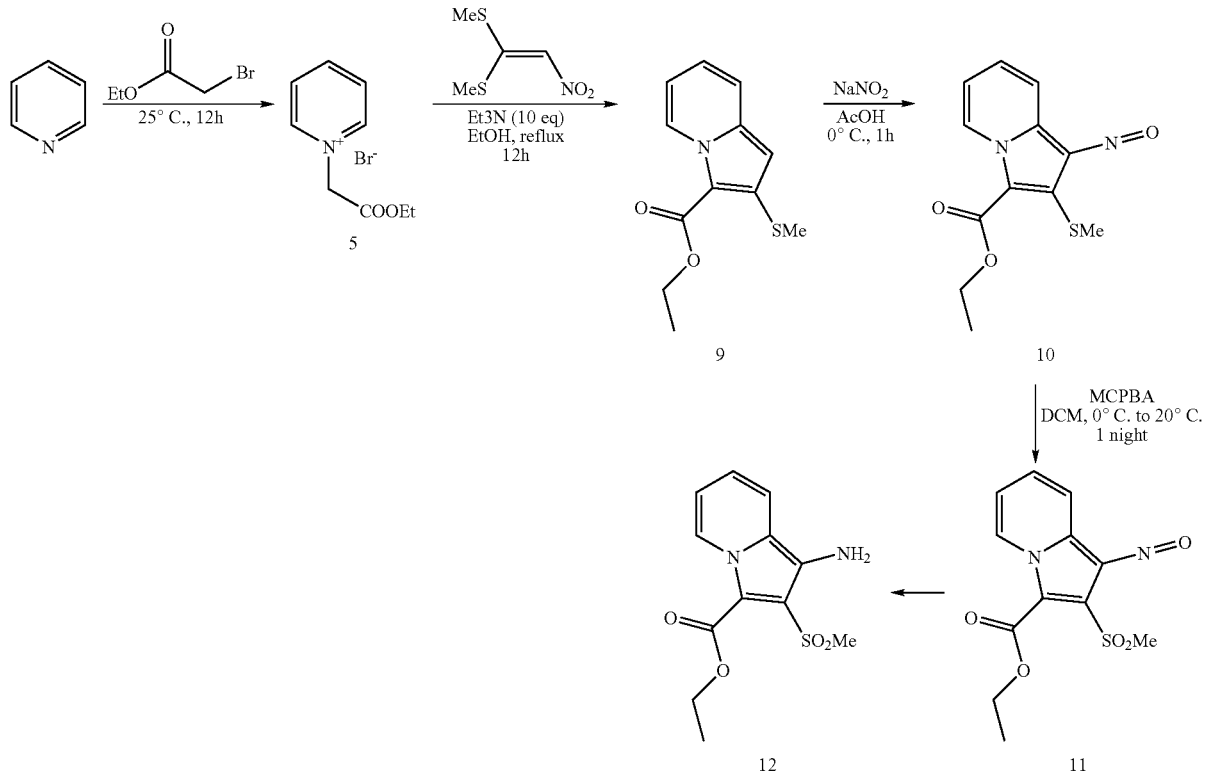

Preparation of Ethyl 2-(methylsulphanyl)-3-indolizinecarboxylate (9). [1989, Journal of Heterocyclic Chemistry, p. 477]

A solution of 1-ethoxycarbonylmethylpyridinium bromide 5 (6.15 g, 25 mmol), 1,1-bis(methylsulphanyl)-2-nitroethylene (8.2 g, 50 mmol) and 25 g of triethylamine in 150 ml of ethanol was heated at reflux for 12 h. Following evaporation of the solvents and of the excess triethylamine, 150 ml of water were added to the residue, and the organic phase was extracted with petroleum ether (75 ml×3). The combined extracts were dried over anhydrous magnesium sulphate, filtered and then concentrated under vacuum. The residual oil was chromatographed on a neutral alumina column, with hexane as the eluting solvent, to give ethyl 2-(methylsulphanyl)-3-indolizinecarboxylate 9 (5.4 g).

Preparation of Ethyl 2-(methylsulphanyl)-1-nitroso-3-indolizinecarboxylate (10).

A solution of 470 mg (2 mmol) of ethyl 2-(methylsulphanyl)-3-indolizinecarboxylate 9 in 10 ml of acetic acid, stirred at 0° C., was admixed dropwise over 10 minutes with a solution of 165 mg of sodium nitrite in 5 ml of water. The reaction mixture was then left with stirring for a further hour. The acidic phase was basified with a solution of 2N NaOH, and then extracted with dichloromethane (25 ml×3). The organic phase was dried over magnesium sulphate, filtered and then concentrated under vacuum to give ethyl 2-(methylsulphanyl)-1-nitroso-3-indolizinecarboxylate 10 (460 mg). m.p: 134-135° C. $^1$H NMR (CDCl$_3$): δ 9.58 (d, J=6.8 Hz, 1H), 8.45 (d, J=8.5 Hz, 1H), 7.70 (t, J=8.2 Hz, 1H), 7.20 (td, J=7.0, 1.1 Hz, 1H), 4.50 (q, J=7.1 Hz, 2H), 3.05 (s, 3H), 1.52 (t, J=7.1 Hz, 3H). $^{13}$C NMR (CDCl$_3$): 161.2, 156.9, 143.4, 135.7, 127.2, 123.7, 118.7, 118.0, 112.9, 61.2, 19.4, 14.4.

Preparation of Ethyl 2-(methylsulphonyl)-1-nitroso-3-indolizinecarboxylate (11).

A stirred solution of ethyl 2-(methylsulphanyl)-1-nitroso-3-indolizinecarboxylate 10 (265 mg, 1 mmol) in dichloromethane (5 mL) at 0° C. was admixed with m-chloroperbenzoic acid (430 mg, 65% strength, 2 eq.) and the reaction mixture was stirred at 25° C. for a night. It was subsequently washed with saturated sodium bisulphite solution (3×5 ml) and then with saturated sodium bicarbonate solution (3×5 ml). The organic phase was dried over magnesium sulphate and then concentrated to give 290 mg of ethyl 2-(methylsulphonyl)-1-nitroso-3-indolizinecarboxylate 11 after recrystallization from methanol. m.p. 143-144° C. $^1$H NMR (CDCl$_3$): δ 9.16 (d, J=7.0 Hz, 1H), 8.49 (d, J=9.1 Hz, 1H), 7.60 (t, J=8.0 Hz, 1H), 7.19 (t, J=7.0 Hz, 1H), 4.58-4.47 (m, 2H), 3.27 (s, 3H), 1.49 (t, J=7.1 Hz, 3H). $^{13}$C NMR (CDCl$_3$): δ 160.0, 136.8, 133.0, 129.7, 127.0, 118.8, 116.8, 115.0, 62.6, 39.7, 14.2.

The preparation of ethyl 2-(methylsulphonyl)-1-amino-3-indolizinecarboxylate 12 from ethyl 2-(methylsulphonyl)-1-nitroso-3-indolizinecarboxylate 11 was performed by a procedure in accordance with that employed in the last step of Example 1.

Example 4

Synthesis of 2-methyl-1-aminoindolizine (14) (Compound A)

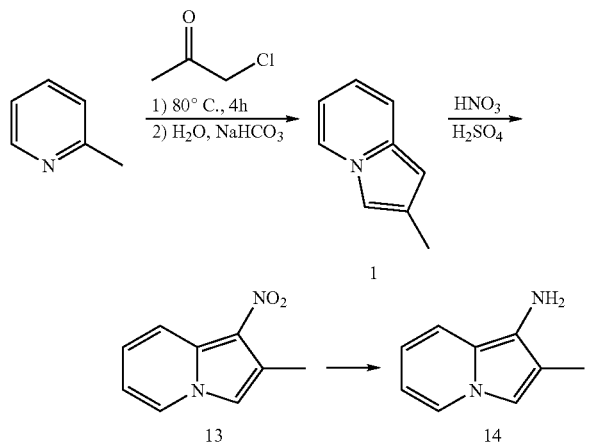

Preparation of 2-methyl-1-nitroindolizine (13).

Nitric acid (5 mL, 70%) was added slowly to a stirred solution of 2-methylindolizine 1 (see preparation of Example 1) (5 g, 38.2 mmol) in concentrated sulphuric acid (15 mL, 96%) at 0° C. After 5 minutes, the brown solution obtained was poured onto crushed ice. The orange precipitate formed was immediately isolated by filtration, washed with copious amounts of water and then dried under vacuum in the presence of $P_2O_5$ for a night to give 2-methyl-1-nitroindolizine 13 (3 g), m.p. 137-139° C. $^1$H NMR (DMSO-$d_6$): δ 8.55 (dt, J=6.7, 1.0 Hz, 1H), 8.20 (d, J=9.1 Hz, 1H), 7.54-7.48 (m, 2H), 7.11 (dt, J=8.0, 1.2 Hz, 1H), 2.47 (d, J=1.0 Hz, 3H). $^{13}$C NMR (DMSO-$d_6$): δ 132.2, 128.0, 127.7, 123.0, 122.8, 117.8, 115.0, 114.7, 12.4.

The preparation of 2-methyl-1-aminoindolizine 14 was performed by reduction of 2-methyl-1-nitroindolizine 13.

Example 5

Synthesis of 2,3-dimethylindolizin-1-ylamine (17) (Compound C)

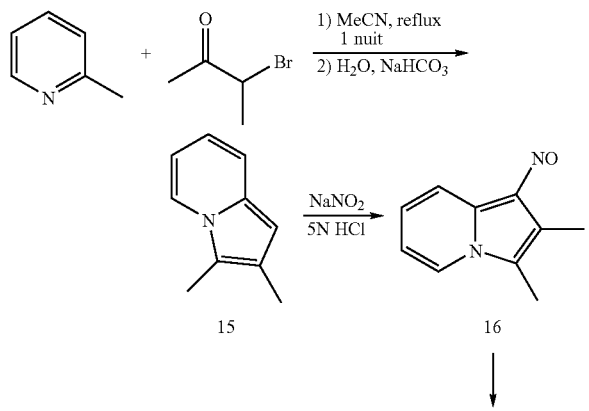

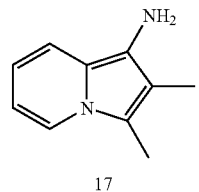

Preparation of 2,3-dimethylindolizine (15) [1962, Journal of the Chemical Society, p. 2627].

A mixture of α-picoline (3 g, 32.3 mmol) and 3-bromobutan-2-one (5 g, 33 mmol) was heated at 80° C. for 8 h. The reaction mixture was poured into a chloroform/water mixture (50:50 mL), decanted and then separated. The aqueous phase was treated with sodium bicarbonate (14 g, 166 mmol) and then distilled to give a mixture of white solid and water. Extraction of the mixture with diethyl ether gave, following removal of the solvents, 4 g of 2,3-dimethylindolizine 15 in the form of white crystals; m.p. 39-40° C. $^1$H NMR (CDCl$_3$): δ 7.60 (d, J=6.9 Hz, 1H), 7.29-7.23 (m, 1H), 7.00-6.55 (m, 1H), 6.48-6.42 (m, 1H), 6.26 (s, 1H), 2.35 (s, 3H), 2.29 (s, 3H).

The preparation of 2,3-dimethylindolizin-1-ylamine 17 from 2,3-dimethylindolizine 15 was performed in the same way as the preparation of the compound 4 from the compound 2 of Example 1.

FORMULATION EXAMPLES

The non-limiting examples below present dyeing compositions in a basic or acidic medium.

For the dyeing compositions in a basic medium, dyeing vehicle 1, with a pH of 9.5, was used:

| Dyeing Vehicle 1 | |
|---|---|
| 96° ethyl alcohol | 20.8 g |
| 35% aqueous sodium metabisulphite solution | 0.23 g as |
| 40% aqueous solution of the pentasodium salt of diethylene-triaminepentaacetic acid | 0.48 g as |
| 60% aqueous solution of $C_8$-$C_{10}$ alkyl-polyglucoside | 3.6 g as |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

[as = active substance]

For the dyeing compositions in an acidic medium, dyeing vehicle 2, with a pH of 7, was used:

| Dyeing Vehicle 2 | |
|---|---|
| 96° ethyl alcohol | 20.8 g |
| 35% aqueous sodium metabisulphite solution | 0.23 g as |
| 40% aqueous solution of the pentasodium salt of diethylene-triaminepentaacetic acid | 0.48 g as |
| 60% aqueous solution of $C_8$-$C_{10}$ alkyl-polyglucoside | 3.6 g as |
| Benzyl alcohol | 2.0 g |
| Polyethylene glycol containing 8 ethylene oxide units | 3.0 g |
| Na$_2$HPO$_4$ | 0.28 g |
| KH$_2$PO$_4$ | 0.46 g |

The compositions of Examples 1 to 8 comprised methyl 2-methyl-1-aminoindolizine-3-carboxylate (Compound B).

At the time of use, each composition was mixed with an equal weight of 20-volumes hydrogen peroxide (6% by weight). This gave a final pH of 9.5 or 7, depending on the vehicle used.

Each mixture obtained was applied to locks of natural grey hair containing 90% white hairs. After 30 minutes' exposure, the locks were rinsed, washed with a standard shampoo, rinsed again and then dried.

Examples 1 to 4 of Dyeing in a Basic Medium pH 9.5

|  | Examples | | | |
|---|---|---|---|---|
|  | 1 | 2 | 3 | 4 |
| Compound B | $10^{-3}$ mol | $10^{-3}$ mol | $10^{-3}$ mol | $10^{-3}$ mol |
| 5-Amino-2-methyl-phenol | $10^{-3}$ mol | | | |
| 1H-Indol-6-ol | | $10^{-3}$ mol | | |
| 2-(2,4-Diamino-phenoxy)ethanol, hydrochloride | | | $10^{-3}$ mol | |
| 3-Amino-2-chloro-6-methyl-phenol, hydrochloride | | | | $10^{-3}$ mol |
| Dyeing vehicle(1) | (*) | (*) | (*) | (*) |
| Demineralized water qs | 100 g | 100 g | 100 g | 100 g |
| Shade observed | violet grey | orange | green-blue | blue grey |

(*) Dyeing vehicle (1): see above

Examples 5 to 8 of Dyeing in an Acidic Medium (pH=7)

|  | Examples | | | |
|---|---|---|---|---|
|  | 5 | 6 | 7 | 8 |
| Compound B | $10^{-3}$ mol | $10^{-3}$ mol | $10^{-3}$ mol | $10^{-3}$ mol |
| Benzene-1,3-diol | $10^{-3}$ mol | | | |
| 5-Amino-2-methyl-phenol | | $10^{-3}$ mol | | |
| 2-(2,4-Diamino-phenoxy)ethanol, hydrochloride | | | $10^{-3}$ mol | |
| 3-Amino-2-chloro-6-methyl-phenol, hydrochloride | | | | $10^{-3}$ mol |
| Dyeing vehicle(2) | (*) | (*) | (*) | (*) |
| Demineralized water qs | 100 g | 100 g | 100 g | 100 g |
| Shade observed | grey | grey | green-blue | blue grey |

(*) Dyeing vehicle (2): see above

The compositions of Examples 9 to 16 comprised 2-methyl-1-aminoindolizine (14) (Compound A):

Example 9 of Dyeing in a Basic Medium (pH 9.5)

|  | Example 9 |
|---|---|
| Compound A | $10^{-3}$ mol |
| 3-Amino-2-chloro-6-methyl-phenol, hydrochloride | $10^{-3}$ mol |
| Dyeing vehicle(1) | (*) |
| Demineralized water qs | 100 g |
| Shade observed | yellow-green grey |

(*) Dyeing vehicle (1): see above

|  | Examples | | | | |
|---|---|---|---|---|---|
|  | 10 | 11 | 12 | 13 | 14 |
| Compound A | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | |
| 5-Amino-2-methylphenol | | $10^{-3}$ mol | | | |
| 1H-Indol-6-ol | | | $10^{-3}$ mol | | |
| 2-Aminopyridin-3-ol | | | | $10^{-3}$ mol | |
| 3,6-Dimethyl-1H-pyrazolo[5,1-c][1,2,4]triazole | | | | | $10^{-3}$ mol |
| Dyeing vehicle (2) | (*) | (*) | (*) | (*) | (*) |
| Demineralized water qs | 100 g | 100 g | 100 g | 100 g | 100 g |
| Shade observed | yellow | brown | orange | orange | orange |

(*) Dyeing vehicle (2): see above

|  | Examples | |
| --- | --- | --- |
|  | 15 | 16 |
| Compound A | $10^{-3}$ mol | $10^{-3}$ mol |
| 2-(2,4-Diaminophenoxy)ethanol, hydrochloride | $10^{-3}$ mol |  |
| 3-Amino-2-chloro-6-methylphenol, hydrochloride |  | $10^{-3}$ mol |
| Dyeing vehicle(2) | (*) | (*) |
| Demineralized water qs | 100 g | 100 g |
| Shade observed | grey | grey |

(*) Dyeing vehicle (2): see above

What is claimed is:

1. At least one chemical entity chosen from aminoindolizines of formula (I) acid addition salts thereof, and solvates thereof:

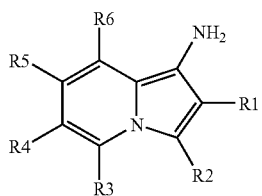

(I)

wherein $R_1$ is a radical chosen from:

linear and branched $C_1$-$C_{10}$ alkyl radicals optionally substituted by at least one group chosen from OH and $OR_{19}$, wherein $R_{19}$ is chosen from linear and branched $C_1$-$C_6$ alkyl radicals optionally substituted by at least one OH radical, sulphur-containing radicals chosen from SR and $SO_2$Me, R being chosen from linear and branched $C_1$-$C_6$ alkyl radicals and aryl radicals, nitrogen-containing radicals chosen from $NH_2$, $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino, $C_1$-$C_6$ mono- and dialkylamino, carboxamido, ureido and guanidinyl groups, and optionally interrupted by an oxygen atom or at least one $N(R_{13})$, $R_{13}$ being chosen from a hydrogen atom and $C_1$-$C_6$ alkyl radicals, it being possible for the radicals $R_7$ and $R_8$ to form, together with the nitrogen atom to which they are attached, a saturated or unsaturated heterocycle containing 5 to 7 ring members, radicals $OR_9$, $R_9$ being chosen from linear and branched $C_1$-$C_6$ alkyl radicals optionally substituted by at least one OH radical, and from linear and branched $C_1$-$C_6$ alkoxy radicals, radicals chosen from COOH, $CONH_2$, $CONHR_{11}$ and $CONR_{11}R_{12}$, wherein $R_{11}$ and $R_{12}$, which are identical or different, are chosen from linear and branched $C_1$-$C_6$ alkyl radicals optionally interrupted by at least one $N(R_{14})$, $R_{14}$ being chosen from a hydrogen atom and $C_1$-$C_6$ alkyl radicals optionally substituted by a hydroxyl group, it being possible for the radicals $R_{11}$ and $R_{12}$ to form, together and with the nitrogen atom to which they are attached, a saturated or unsaturated heterocycle containing 5 to 7 ring members, $R_2$ is a radical chosen from:

linear and branched $C_1$-$C_6$ alkyl radicals, hydrogen atoms, radicals chosen from COOH, CN, $CF_3$ and alkoxycarbonyl $COOR_{10}$, $R_{10}$ being chosen from linear and branched $C_1$-$C_6$ alkyl radicals, and aryl and heteroaryl radicals, radicals chosen from $CONH_2$, $CONHR_{11}$ and $CONR_{11}R_{12}$, radicals $OR_9$, and radicals SR, SOR and $SO_2R$, wherein R, $R_9$, $R_{11}$ and $R_{12}$ are as defined above, $R_3$, $R_4$, $R_5$ and $R_6$, independently of one another, are chosen from:

aryl, heteroaryl and linear and branched $C_1$-$C_6$ alkyl radicals optionally interrupted by at least one entity chosen from $N(R_{13})$ and oxygen, the radicals $OR_9$, hydrogen atoms, halogens chosen from fluorine, chlorine and bromine, nitrogen-containing radicals chosen from $NH_2$, $NHR_7$ and $NR_7R_8$, and COOH and CN radicals and alkoxycarbonyl radicals $COOR_{10}$, wherein $R_7$, $R_8$, $R_9$ and $R_{10}$ are as defined above, with the proviso that not more than one of the radicals $R_1$, $R_3$, $R_4$, $R_5$ and $R_6$ is a nitrogen-containing radical chosen from $NH_2$, $NHR_7$ and $NR_7R_8$.

2. The at least one chemical entity according to claim 1, wherein the radical $R_1$ is chosen from:

linear and branched $C_1$-$C_{10}$ alkyl radicals, the sulphur-containing radical $SO_2$Me, nitrogen-containing radicals chosen from $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino and $C_1$-$C_6$ mono- and dialkylamino groups.

3. The at least one chemical entity according to claim 2, wherein the $R_1$ is chosen from $C_1$-$C_4$ alkyl radicals.

4. The at least one chemical entity according to claim 2, wherein $R_7$ and $R_8$, which are identical or different, are chosen from linear and branched $C_1$-$C_6$ alkyl radicals optionally substituted by at least one entity chosen from hydroxyl, $C_1$-$C_4$ mono- and dialkylamino groups.

5. The at least one chemical entity according to claim 2, wherein the radical $R_1$ is chosen from: —$CH_3$, —$SO_2CH_3$, —$NH(CH_3)$, —$N(CH_2CH_2OH)_2$, —$N(CH_3)_2$, —$NH(CH_2CH_2OH)$, —$NH(CH_2CH_2N(CH_3)_2)$, —$NH(CH_2CH_3)$, and —$NH(CH_2CH_2CH_2N(CH_3)_2)$.

6. The at least one chemical entity according to claim 1, wherein the radical $R_2$ is chosen from:

linear and branched $C_1$-$C_6$ alkyl radicals, hydrogen atoms, radicals chosen from COOH, CN, $CF_3$ and alkoxycarbonyl $COOR_{10}$, $R_{10}$ being chosen from linear and branched $C_1$-$C_6$ alkyl radicals, radicals chosen from $CONH_2$, $CONHR_{11}$ and $CONR_{11}R_{12}$, the radicals $OR_9$, and the radicals SR and $SO_2R$, wherein $R_9$, $R_{10}$, $R_{11}$ and R are defined as in claim 1.

7. The at least one chemical entity according to claim 6, wherein the radical $R_2$ is chosen from $C_1$-$C_4$ alkyl radicals.

8. The at least one chemical entity according to claim 1, wherein the radical $R_2$ is chosen from a hydrogen atom and —$CH_3$, —$COOCH_3$, —$COOCH_2CH_3$, —CN, —$CF_3$, —$CONH(CH_2CH_3)$, —$CONH(CH_2CH_2CH_2N(CH_3)_2)$, —CON(CH$_3$)$_2$, —CONH(CH$_2$CH$_2$OH), —CONH$_2$, —OCH$_3$, —SCH$_3$, and –SO$_2$CH$_3$ radicals.

9. The at least one chemical entity according to claim 1, wherein the radicals R$_3$, R$_4$, R$_5$ and R$_6$, independently of one another, are chosen from:

hydrogen atoms, the radicals OR$_9$, with R$_9$ being a C$_1$-C$_4$ alkyl radical, and the radical —NH$_2$, with the proviso that not more than one of the radicals R$_1$, R$_3$, R$_4$, R$_5$ and R$_6$ is an —NH$_2$ radical.

10. The at least one chemical entity according to claim 9, wherein the radical OR$_9$ is OCH$_3$.

11. The at least one chemical entity according to claim 1 chosen from:

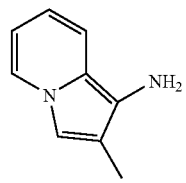

A

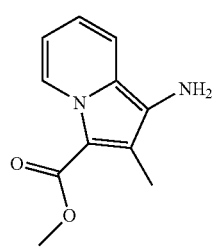

B

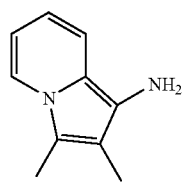

C

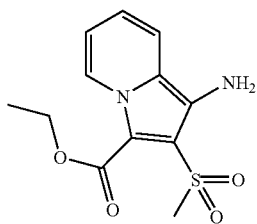

D

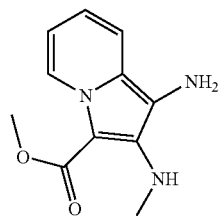

E

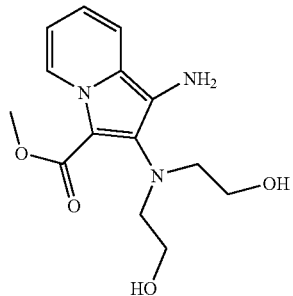

F

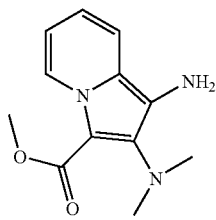

G

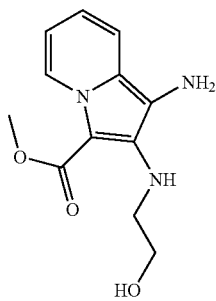

H

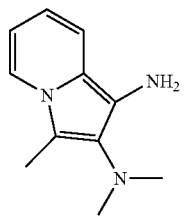

I

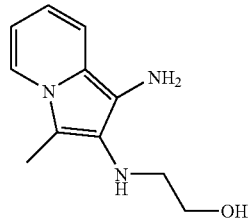

J

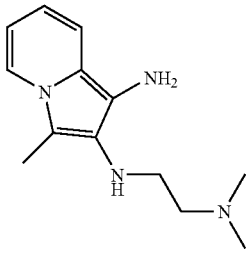

K

-continued
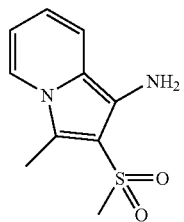
L
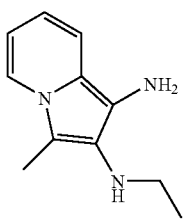
M
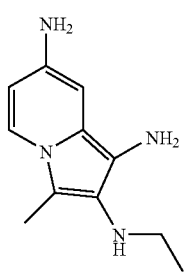
N
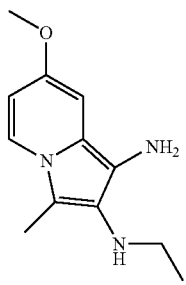
O
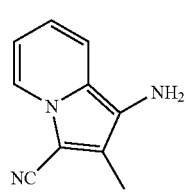
P
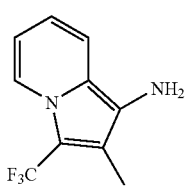
Q
-continued
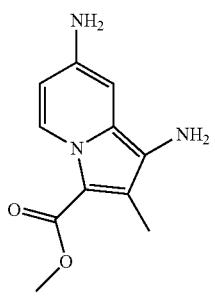
R
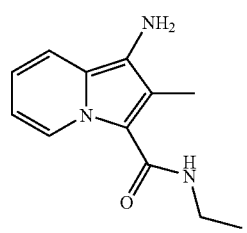
S
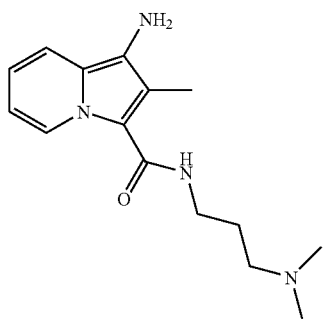
T
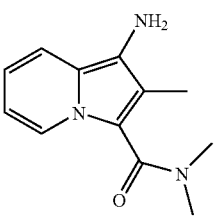
U
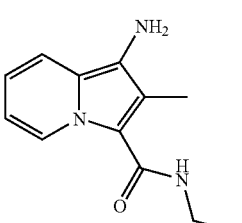
V
W
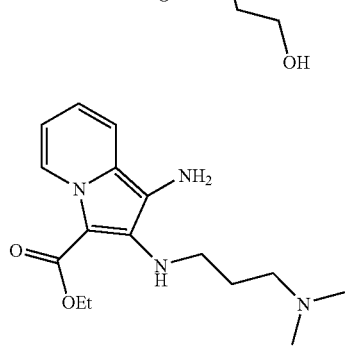

-continued

X

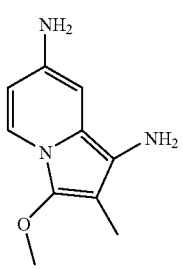
Y

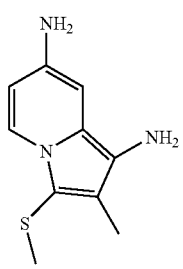
Z

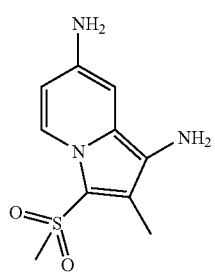
AA

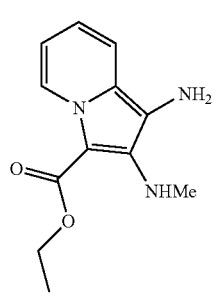
AB acid addition salts thereof, and solvates thereof.

12. A cosmetic dyeing composition comprising, in a medium appropriate for dyeing, at least one chemical entity chosen from aminoindolizines of formula (I), acid addition salts thereof, and solvates thereof:

(I)

wherein $R_1$ is a radical chosen from:
linear and branched $C_1$-$C_{10}$ alkyl radicals optionally substituted by at least one group chosen from OH and $OR_{19}$, wherein $R_{19}$ is chosen from linear and branched $C_1$-$C_6$ alkyl radicals optionally substituted by at least one OH radical, sulphur-containing radicals chosen from SR and $SO_2Me$, R being chosen from linear and branched $C_1$-$C_6$ alkyl radicals and aryl radicals, nitrogen-containing radicals chosen from $NH_2$, $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino, $C_1$-$C_6$ mono- and dialkylamino, carboxamido, ureido and guanidinyl groups, and optionally interrupted by an oxygen atom or at least one $N(R_{13})$, $R_{13}$ being chosen from a hydrogen atom and $C_1$-$C_6$ alkyl radicals, it being possible for the radicals $R_7$ and $R_8$ to form, together with the nitrogen atom to which they are attached, a saturated or unsaturated heterocycle containing 5 to 7 ring members, radicals $OR_9$, $R_9$ being chosen from linear and branched $C_1$-$C_6$ alkyl radicals optionally substituted by at least one OH radical, and from linear and branched $C_1$-$C_6$ alkoxy radicals, radicals chosen from COOH, $CONH_2$, $CONHR_{11}$ and $CONR_{11}R_{12}$, wherein $R_{11}$ and $R_{12}$, which are identical or different, are chosen from linear and branched $C_1$-$C_6$ alkyl radicals optionally interrupted by at least one $N(R_{14})$, $R_{14}$ being chosen from a hydrogen atom and $C_1$-$C_6$ alkyl radicals optionally substituted by a hydroxyl group, it being possible for the radicals $R_{11}$ and $R_{12}$ to form, together and with the nitrogen atom to which they are attached, a saturated or unsaturated heterocycle containing 5 to 7 ring members, $R_2$ is a radical chosen from:
linear and branched $C_1$-$C_6$ alkyl radicals,
hydrogen atoms,
radicals chosen from COOH, CN, $CF_3$ and alkoxycarbonyl $COOR_{10}$, $R_{10}$ being chosen from linear and branched $C_1$-$C_6$ alkyl radicals, and aryl and heteroaryl radicals,
radicals chosen from $CONH_2$, $CONHR_{11}$ and $CONR_{11}R_{12}$,
radicals $OR_9$, and
radicals SR, SOR and $SO_2R$,
wherein R, $R_9$, $R_{11}$ and $R_{12}$ are as defined above, $R_3$, $R_4$, $R_5$ and $R_6$, independently of one another, are chosen from:
aryl, heteroaryl and linear and branched $C_1$-$C_6$ alkyl radicals optionally interrupted by at least one entity chosen from $N(R_{13})$ and oxygen,
the radicals $OR_9$,
hydrogen atoms,
halogens chosen from fluorine, chlorine and bromine, nitrogen-containing radicals chosen from $NH_2$, $NHR_7$ and $NR_7R_8$, and COOH and CN radicals and alkoxycarbonyl radicals $COOR_{10}$, where $R_7$, $R_8$, $R_9$ and $R_{10}$ are as defined above, with the proviso that not more than one of the radicals $R_1$, $R_3$, $R_4$, $R_5$ and $R_6$ is a nitrogen-containing radical chosen from $NH_2$, $NHR_7$ and $NR_7R_8$.

13. The cosmetic dyeing composition according to claim 12, wherein the at least one chemical entity is present in an amount ranging from 0.0001% to 20% by weight, relative to the total weight of the composition.

14. The cosmetic dyeing composition according to claim 13, wherein the at least one chemical entity is present in an amount ranging from 0.005% to 6% by weight, relative to the total weight of the composition.

15. The cosmetic dyeing composition according to claim 12, wherein the medium appropriate for dyeing is water, or comprises a mixture of water and at least one organic solvent.

16. The cosmetic dyeing composition according to claim 15, wherein the at least one organic solvent is chosen from branched and unbranched lower $C_1$-$C_4$ alcohols, polyols, propylene glycol, propylene glycol monomethyl ether, diethylene glycol monoethyl ether and monomethyl ether, glycerol, and aromatic alcohols.

17. The cosmetic dyeing composition according to claim 16, wherein the at least one organic solvent is chosen from ethanol, isopropanol, 2-butoxyethanol, benzyl alcohol and phenoxyethanol.

18. The cosmetic dyeing composition according to claim 12, wherein it further comprises at least one oxidation coupler.

19. The cosmetic dyeing composition according to claim 12, wherein it further comprises at least one additional oxidation base other than the at least one chemical entity, and wherein the at least one additional oxidation base is chosen from para-phenylenediamines, bis-phenylalkylenediamines, para-aminophenols, ortho-aminophenols, heterocyclic bases and the addition salts thereof.

20. The cosmetic dyeing composition according to claim 12, wherein it further comprises at least one dye chosen from cationic and natural direct dye.

21. The cosmetic dyeing composition according to claim 12, wherein it further comprises at least one cosmetic adjuvant chosen from antioxidants, penetrants, sequestrants, perfumes, buffers, dispersants, surfactants, conditioning agents, film formers, polymers, ceramides, preservatives, pearlizing agents, opacifying agents, vitamins, and provitamins.

22. The cosmetic dyeing composition according to claim 12, wherein it is a ready-to-use composition further comprising at least one oxidizing agent chosen from hydrogen peroxide, urea peroxide, alkali metal bromides, persalts, peracids and oxidase enzymes.

23. A method of dyeing keratin fibers, comprising
applying to the keratin fibers at least one cosmetic dyeing composition and
applying to the keratin fibers at least one oxidizing agent, before, simultaneously with, or after the at least one cosmetic dyeing composition, and
leaving said compositions on the fibers for a time sufficient to develop the desired coloration,
wherein said at least one cosmetic dyeing composition comprises, in a medium appropriate for dyeing, at least one chemical entity chosen from aminoindolizines of formula (I), acid addition salts thereof, and solvates thereof:

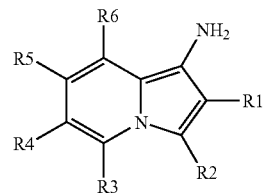

(I)

wherein $R_1$ is a radical chosen from:

linear and branched $C_1$-$C_{10}$ alkyl radicals optionally substituted by at least one group chosen from OH and $OR_{19}$, wherein $R_{19}$ is chosen from linear and branched $C_1$-$C_6$ alkyl radicals optionally substituted by at least one OH radical, sulphur-containing radicals chosen from SR and $SO_2Me$, R being chosen from linear and branched $C_1$-$C_6$ alkyl radicals and aryl radicals, nitrogen-containing radicals chosen from $NH_2$, $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino, $C_1$-$C_6$ mono- and dialkylamino, carboxamido, ureido and guanidinyl groups, and optionally interrupted by an oxygen atom or at least one $N(R_{13})$, $R_{13}$ being chosen from a hydrogen atom and $C_1$-$C_6$ alkyl radicals, it being possible for the radicals $R_7$ and $R_8$ to form, together with the nitrogen atom to which they are attached, a saturated or unsaturated heterocycle containing 5 to 7 ring members, radicals $OR_9$, $R_9$ being chosen from linear and branched $C_1$-$C_6$ alkyl radicals optionally substituted by at least one OH radical, and from linear and branched $C_1$-$C_6$ alkoxy radicals, radicals chosen from COOH, $CONH_2$, $CONHR_{11}$ and $CONR_{11}R_{12}$, wherein $R_{11}$ and $R_{12}$, which are identical or different, are chosen from linear and branched $C_1$-$C_6$ alkyl radicals optionally interrupted by at least one $N(R_{14})$, $R_{14}$ being chosen from a hydrogen atom and $C_1$-$C_6$ alkyl radicals optionally substituted by a hydroxyl group, it being possible for the radicals $R_{11}$ and $R_{12}$ to form, together and with the nitrogen atom to which they are attached, a saturated or unsaturated heterocycle containing 5 to 7 ring members, $R_2$ is a radical chosen from:

linear and branched $C_1$-$C_6$ alkyl radicals, hydrogen atoms, radicals chosen from COOH, CN, $CF_3$ and alkoxycarbonyl $COOR_{10}$, $R_{10}$ being chosen from linear and branched $C_1$-$C_6$ alkyl radicals, and aryl and heteroaryl radicals, radicals chosen from $CONH_2$, $CONHR_{11}$ and $CONR_{11}R_{12}$, radicals $OR_9$, and radicals SR, SOR and $SO_2R$, wherein R, $R_9$, $R_{11}$ and $R_{12}$ are as defined above, $R_3$, $R_4$, $R_5$ and $R_6$, independently of one another, are chosen from:

aryl, heteroaryl and linear and branched $C_1$-$C_6$ alkyl radicals optionally interrupted by at least one entity chosen from $N(R_{13})$ and oxygen, the radicals $OR_9$, hydrogen atoms, halogens chosen from fluorine, chlorine and bromine, nitrogen-containing radicals chosen from $NH_2$, $NHR_7$ and $NR_7R_8$, and COOH and CN radicals and alkoxycarbonyl radicals $COOR_{10}$, where $R_7$, $R_8$, $R_9$ and $R_{10}$ are as defined above, with the proviso that not more than one of the radicals $R_1$, $R_3$, $R_4$, $R_5$ and $R_6$ is a nitrogen-containing radical chosen from $NH_2$, $NHR_7$ and $NR_7R_8$.

24. The method of dyeing keratin fibers according to claim 23, wherein the cosmetic dyeing composition is a ready-to-use composition comprising at least one oxidizing agent chosen from hydrogen peroxide, urea peroxide, alkali metal bromides, persalts, peracids and oxidase enzymes.

25. A multi-compartment kit, comprising at least one first compartment containing at least one cosmetic composition for dyeing keratin fibers, and at least one second compartment containing at least one oxidizing agent, wherein said at least one cosmetic composition comprises, in a medium appropriate for dyeing, at least one at least one chemical entity chosen from aminoindolizines of formula (I), acid addition salts thereof, and solvates thereof:

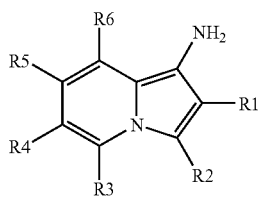

(I)

wherein $R_1$ is a radical chosen from:

linear and branched $C_1$-$C_{10}$ alkyl radicals optionally substituted by at least one group chosen from OH and $OR_{19}$, wherein $R_{19}$ is chosen from linear and branched $C_1$-$C_6$ alkyl radicals optionally substituted by at least one OH radical, sulphur-containing radicals chosen from SR and $SO_2Me$, R being chosen from linear and branched $C_1$-$C_6$ alkyl radicals and aryl radicals, nitrogen-containing radicals chosen from $NH_2$, $NHR_7$ and $NR_7R_8$, wherein $R_7$ and $R_8$, which are identical or different, are chosen from linear and branched $C_1$-$C_6$ alkyl radicals optionally substituted by at least one entity chosen from hydroxyl, amino, $C_1$-$C_6$ mono- and dialkylamino, carboxamido, ureido and guanidinyl groups, and optionally interrupted by an oxygen atom or at least one $N(R_{13})$, $R_{13}$ being chosen from a hydrogen atom and $C_1$-$C_6$ alkyl radicals, it being possible for the radicals $R_7$ and $R_8$ to form, together with the nitrogen atom to which they are attached, a saturated or unsaturated heterocycle containing 5 to 7 ring members, radicals $OR_9$, $R_9$ being chosen from linear and branched $C_1$-$C_6$ alkyl radicals optionally substituted by at least one OH radical, and from linear and branched $C_1$-$C_6$ alkoxy radicals, radicals chosen from COOH, $CONH_2$, $CONHR_{11}$ and $CONR_{11}R_{12}$, wherein $R_{11}$ and $R_{12}$, which are identical or different, are chosen from linear and branched $C_1$-$C_6$ alkyl radicals optionally interrupted by at least one $N(R_{14})$, $R_{14}$ being chosen from a hydrogen atom and $C_1$-$C_6$ alkyl radicals optionally substituted by a hydroxyl group, it being possible for the radicals $R_{11}$ and $R_{12}$ to form, together and with the nitrogen atom to which they are attached, a saturated or unsaturated heterocycle containing 5 to 7 ring members, $R_2$ is a radical chosen from:

linear and branched $C_1$-$C_6$ alkyl radicals, hydrogen atoms, radicals chosen from COOH, CN, $CF_3$ and alkoxycarbonyl $COOR_{10}$, $R_{10}$ being chosen from linear and branched $C_1$-$C_6$ alkyl radicals, and aryl and heteroaryl radicals, radicals chosen from $CONH_2$, $CONHR_{11}$ and $CONR_{11}R_{12}$, radicals $OR_9$, and radicals SR, SOR and $SO_2R$, wherein R, $R_9$, $R_{11}$ and $R_{12}$ are as defined above, $R_3$, $R_4$, $R_5$ and $R_6$, independently of one another, are chosen from:

aryl, heteroaryl and linear and branched $C_1$-$C_6$ alkyl radicals optionally interrupted by at least one entity chosen from $N(R_{13})$ and oxygen, the radicals $OR_9$, hydrogen atoms, halogens chosen from fluorine, chlorine and bromine, nitrogen-containing radicals chosen from $NH_2$, $NHR_7$ and $NR_7R_8$, and COOH and CN radicals and alkoxycarbonyl radicals $COOR_{10}$, where $R_7$, $R_8$, $R_9$ and $R_{10}$ are as defined above, with the proviso that not more than one of the radicals $R_1$, $R_3$, $R_4$, $R_5$ and $R_6$ is a nitrogen-containing radical chosen from $NH_2$, $NHR_7$ and $NR_7R_8$.

* * * * *